US008440185B2

(12) United States Patent
Chen et al.

(10) Patent No.: US 8,440,185 B2
(45) Date of Patent: May 14, 2013

(54) COMPOSITIONS AND METHODS FOR THE TREATMENT OF IMMUNOLOGIC DISORDERS

(75) Inventors: Lieping Chen, Sparks Glencoe, MD (US); Koji Tamada, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 141 days.

(21) Appl. No.: 11/964,599

(22) Filed: Dec. 26, 2007

(65) Prior Publication Data

US 2008/0187542 A1  Aug. 7, 2008

Related U.S. Application Data

(60) Provisional application No. 60/877,176, filed on Dec. 26, 2006.

(51) Int. Cl.
*A61K 39/395* (2006.01)

(52) U.S. Cl.
USPC ........................................ 424/130.1

(58) Field of Classification Search .................. None
See application file for complete search history.

(56) References Cited

U.S. PATENT DOCUMENTS

| | | | |
|---|---|---|---|
| 4,634,664 A | 1/1987 | Oestberg | |
| 4,634,666 A | 1/1987 | Engleman et al. | |
| 4,650,764 A | 3/1987 | Temin et al. | |
| 4,769,330 A | 9/1988 | Paoletti et al. | |
| 4,861,719 A | 8/1989 | Miller | |
| 4,925,673 A | 5/1990 | Steiner et al. | |
| 4,980,289 A | 12/1990 | Temin et al. | |
| 5,013,556 A | 5/1991 | Woodle et al. | |
| 5,120,727 A | 6/1992 | Kao et al. | |
| 5,124,263 A | 6/1992 | Temin et al. | |
| 5,155,020 A | 10/1992 | Paoletti | |
| 5,162,333 A | 11/1992 | Failli et al. | |
| 5,175,099 A | 12/1992 | Wills | |
| 5,202,332 A | 4/1993 | Hughes et al. | |
| 5,204,243 A | 4/1993 | Paoletti | |
| 5,225,336 A | 7/1993 | Paoletti | |
| 5,225,539 A | 7/1993 | Winter | |
| 5,240,846 A | 8/1993 | Collins et al. | |
| 5,278,056 A | 1/1994 | Bank et al. | |
| 5,304,489 A | 4/1994 | Rosen | |
| 5,385,908 A | 1/1995 | Nelson et al. | |
| 5,484,790 A | 1/1996 | Failli et al. | |
| 5,530,006 A | 6/1996 | Waranis et al. | |
| 5,530,101 A | 6/1996 | Queen et al. | |
| 5,545,806 A | 8/1996 | Lonberg et al. | |
| 5,559,112 A | 9/1996 | Skotnicki et al. | |
| 5,565,332 A | 10/1996 | Hoogenboom et al. | |
| 5,567,709 A | 10/1996 | Skotnicki et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,693,761 A | 12/1997 | Queen et al. | |
| 5,693,762 A | 12/1997 | Queen et al. | |
| 5,733,743 A | 3/1998 | Johnson et al. | |
| 5,736,142 A | 4/1998 | Sette et al. | |
| 5,741,957 A | 4/1998 | Deboer et al. | |
| 5,770,429 A | 6/1998 | Lonberg et al. | |
| 5,780,462 A | 7/1998 | Lee et al. | |
| 5,789,650 A | 8/1998 | Lonberg et al. | |
| 5,814,318 A | 9/1998 | Lonberg et al. | |
| 5,837,242 A | 11/1998 | Holliger et al. | |
| 5,849,992 A | 12/1998 | Meade et al. | |
| 5,858,657 A | 1/1999 | Winter et al. | |
| 5,871,907 A | 2/1999 | Winter et al. | |
| 5,874,299 A | 2/1999 | Lonberg et al. | |
| 5,877,218 A | 3/1999 | Herzig et al. | |
| 5,877,397 A | 3/1999 | Lonberg et al. | |
| 5,989,591 A | 11/1999 | Nagi | |
| 6,015,809 A | 1/2000 | Zhu et al. | |
| 6,051,385 A * | 4/2000 | Fuller et al. | ............ 435/7.1 |

FOREIGN PATENT DOCUMENTS

| | | |
|---|---|---|
| WO | WO 90/07861 | 7/1990 |
| WO | WO 91/10741 | 7/1991 |
| WO | WO 91/17271 | 11/1991 |
| WO | WO 92/01047 | 1/1992 |
| WO | WO 92/20791 | 11/1992 |
| WO | WO 93/01222 | 1/1993 |
| WO | WO 95/04738 | 2/1995 |
| WO | WO 95/07707 | 3/1995 |
| WO | WO 95/16691 | 6/1995 |
| WO | WO 95/22972 | 8/1995 |
| WO | WO 97/03687 | 2/1997 |
| WO | WO 97/17613 | 5/1997 |
| WO | WO 97/17614 | 5/1997 |
| WO | WO 98/23635 | 6/1998 |
| WO | WO 98/56401 | 12/1998 |
| WO | WO 00/01385 | 1/2000 |
| WO | WO 01/00228 | 1/2001 |
| WO | WO 03/066834 | 8/2003 |

OTHER PUBLICATIONS

Huang Z., Pharmacology and Therapeutics, 2000, 86: 201-215.*

(Continued)

*Primary Examiner* — Ilia Ouspenski

(74) *Attorney, Agent, or Firm* — Johns Hopkins Technology Transfer

(57) ABSTRACT

Compositions and methods for preventing, reducing or inhibiting immunologic disorders are provided. Suitable compositions include one or more LIGHT-HVEM antagonists. LIGHT-HVEM antagonists include compounds that inhibit, reduce, or block the biological activity or expression of LIGHT and/or HVEM. LIGHT-HVEM antagonists can reduce or inhibit the binding of LIGHT to HVEM, but do not significantly modulate the binding of LTβ to LTβR. Suitable compositions include antibodies and antibody fragments, decoy polypeptides, small molecule inhibitors and inhibitory nucleic acids. Methods for using LIGHT-HVEM antagonists to reduce or inhibit T cell activation and survival are also provided. Therapeutic uses for LIGHT-HVEM antagonists to prevent or treat immunologic diseases and disorders including graft rejection, graft-versus-host disease, inflammatory immune responses, and autoimmune disorders are provided.

11 Claims, 12 Drawing Sheets

OTHER PUBLICATIONS

Blazer et al., J. Immunol., 1996, 157: 3250-3259.*
Anand et al., J. Clin. Investigation, 2006, 116: 1045-1051.*
Acsadi, et al., "Direct gene transfer and expression into rat heart in vivo", *The New Biologist*, 3:71-81 (1991).
Aggarwal, "Signalling pathways of the TNF superfamily: a double-edged sword", *Nat. Rev. Immunol.*, 3(9):745-56 (2003).
Aldovini, et al., "Humoral and cell-mediated immune responses to live recombinant BCG-HIV vaccines", *Nature*, 351(6326):479-482 (1991).
Alexander, et al., "Development of high potency universal DR-restricted helper epitopes by modification of high affinity DR-blocking peptides", *Immunity*, 1:751-761 (1994).
Alimzhanov, et al., "Abnormal development of secondary lymphoid tissues in lymphotoxin beta-deficient mice", *Proc. Natl. Acad. Sci. U.S.A.*, 94:9302-9307 (1997).
Anand, et al., "Essential role of TNF family molecule LIGHT as a cytokine in the pathogenesis of hepatitis", *J. Clin. Invest.*, 116:1045-1051 (2006).
Anderson, "Human gene therapy", *Science*, 256:808-813 (1992).
Blazar, et al., "Bone marrow transplantation and approaches to avoid graft-versus-host disease (GVHD)", *Philos. Trans. R. Soc. Lond. B Biol. Sci.*, 360:1747-1767 (2005).
Burke, et al., "The influence of adjuvant on the therapeutic efficacy of a recombinant genital herpes vaccine", *J. Inf. Dis.*, 170,1110-19 (1994).
Chakrabarti, et al., "Vaccinia virus expression vector: coexpression of beta-galactosidase provides visual screening of recombinant virus plaques", *Molec. Cell. Biol.*, 5:3403-3409 (1985).
Chicz, et al., "Specificity and promiscuity among naturally processed peptides bound to HLA-DR alleles", *J. Exp. Med.*, 178:27-47 (1993).
Co, et al., "Chimeric and humanized antibodies with specificity for the CD33 antigen", *J. Immunol.*, 148:1149-54 (1992).
Cone, et al, High-efficiency gene transfer into mammalian cells: generation of helper-free recombinant retrovirus with broad mammalian host range', *Proc. Natl. Acad. Sci. USA*, 81:6349-6353 (1984).
Crystal, "Gene therapy strategies for pulmonary disease", *Amer. J. Med.* 92(6A):44S-52S (1992).
Falk, et al., "Pool sequencing of natural HLA-DR, DQ, and DP ligands reveals detailed peptide motifs, constraints of processing, and general rules", *Immunogenetics*, 39:230-242 (1994).
Falkner, et al., "pUV I: a new vaccinia virus insertion and expression vector", *Nucl. Acids Res*, 15:7192 (1987).
Fink, et al., Monoclonal antibodies as diagnostic reagents for the identification and characterization of human tumor antigens', *Prog. Clin. Pathol.*, 9:121-33 (1984).
Fuerst, et al., "Transfer of the inducible lac repressor/operator system from *Escherichia coli* to a vaccinia virus expression vector", *Proc. Natl. Acad. Sci. USA*, 86:2549-2553 (1989).
Futterer, et al., "The lymphotoxin beta receptor controls organogenesis and affinity maturation in peripheral lymphoid tissues", Immunity, 9:59-70 (1998).
Gommerman, et al., "Lymphotoxin/light, lymphoid microenvironments and autoimmune disease", Nat. Rev. Immunol., 3:642-655 (2003).
Guatelli, et al., "Isothermal, in vitro amplification of nucleic acids by a multienzyme reaction modeled after retroviral replication", *Proc. Natl. Acad. Sci. USA*, 87:1874-1878 (1990).
Hammer, et al., "Promiscuous and allele-specific anchors in HLA-DR-binding peptides", *Cell*, 74:197-203 (1993).
Hatzoglou, et al., "Hepatic gene transfer in animals using retroviruses containing the promoter from the gene for phosphoenolpyruvate carboxykinase", *J. Biol. Chem.*, 265(28):17285-93 (1990).
Henikoff and Henikoff, Amino acid substitution matrices from protein blocks', *Proc. Natl. Acad. Sci. U.S.A.*, 89:10915-10919 (1992).
Hock, et al., "Retrovirus-mediated transfer and expression of drug resistance genes in human haematopoietic progenitor cells", *Nature*, 320:275-277 (1986).
Hoiseth & Stocker, "Aromatic-dependent *Salmonella typhimurium* are non-virulent and effective as live vaccines", *Nature*, 291,238-239 (1981).
Huse, et al., "Generation of a large combinatorial library of the immunoglobulin repertoire in phage lambda", *Science*, 246:1275-1281 (1989).
Iizuka, et al., "Requirement for membrane lymphotoxin in natural killer cell development", *Proc. Natl. Acad. Sci. U.S.A.*, 96:6336-6340 (1999).
Ikonomidis, et al., "Delivery of a viral antigen to the class I processing and presentation pathway by Listeria monocytogenes", *J. Exp. Med.*, 180:2209-2218 (1994).
Johnston, et al., In Vitro *Cell. Dev. Biol.*, 27:11-14 (1991).
Kabashima, et al., "Intrinsic lymphotoxin-beta receptor requirement for homeostasis of lymphoid tissue dendritic cells", *Immunity*, 22:439-450 (2005).
Kim, et al., "LIGHT is involved in the pathogenesis of rheumatoid arthritis by inducing the expression of pro-inflammatory cytokines and MMP-9 in macrophages." *Immunology*, 114(2):272-9 (2005).
Kohler and Milstein, "Continuous cultures of fused cells secreting antibody of predefined specificity", *Nature*, 256(5517):495-97 (1975).
Kohn, et al., "Gene therapy for genetic diseases", *Cancer Invest.*, 7(2):179-192 (1989).
Koleko, et al., Persistent gene expression after retroviral gene transfer into liver cells in vivo, *Human Gene Therapy*, 2(1):27-32 (1991).
Kostelny, et al., "Formation of a bispecific antibody by the use of leucine zippers", *J. Immunol.*, 148:1547-1553 (1992).
Lee, et al., "Tumor necrosis factor receptor superfamily 14 is involved in atherogenesis by inducing proinflammatory cytokines and matrix metalloproteinases", *Arterioscler. Thromb. Vasc. Biol.*, 21(12):2004-10 (2001).
Lewis, *Genetic Engineering News*, 12:1 (1992).
Liu, et al., "LIGHT-deficiency impairs CD8+ T cell expansion, but not effector function", *Int. Immunol.*, 15:861-870 (2003).
Mackay, et al., "Lymphotoxin but not tumor necrosis factor functions to maintain splenic architecture and humoral responsiveness in adult mice", *Eur. J. Immunol.*, 27:2033-2042 (1997).
Mann, et al., "Construction of a retrovirus packaging mutant and its use to produce helper-free defective retrovirus", *Cell*, 33:153-159 (1983).
Mathiowitz and Langer, "Polyanhydride microspheres as drug carriers I. Hot-melt microencapsulation ", *J. Controlled Release*, 5:13-22 (1987).
Mathiowitz, et al., "Polyanhydride microspheres as drug carriers II. Microencapsulation by solvent removal", *J. Appl. Polymer Sci.*, 35:755-774 (1988).
Mathiowitz, et al., "Novel microcapsules for delivery systems", *Reactive Polymers*, 6:275-283 (1987).
Mauri, et al., "Light, a new member of the TNF superfamily, and lymphotoxin alpha are ligands for herpesvirus entry mediator" *Immunity*, 8(1):21-30 (1998).
Mclachlin, et al., "Retroviral-mediated gene transfer", *Prog. Nuc. Acid Res. Molec. Biol.* 38:91-135 (1990).
Miller, et al., "Generation of helper-free amphotropic retroviruses that transduce a dominant-acting, methotrexate-resistant dihydrofolate reductase gene", *Molec. Cell. Biol.*, 5:431-437 (1985).
Miller, et al., "Redesign of retrovirus packaging cell lines to avoid recombination leading to helper virus production", *Molec. Cell. Biol.*, 6:2895-2902 (1986).
Miller, et al., "Gene transfer by retrovirus vectors occurs only in cells that are actively replicating at the time of infection", *Mol. Cell. Biol.*, 10:4239 (1990).
Miller, "Human gene therapy comes of age", *Nature*, 357:455-460 (1992).
Moreland, et al., "Treatment of rheumatoid arthritis with a recombinant human tumor necrosis factor receptor (p75)-Fc fusion protein", *N. Engl. J. Med.*, 337:141-147 (1997).
Moss, et al., "Use of vaccinia virus as an infectious molecular cloning and expression vector", *Gene Amplif Anal*, 3:201-213 (1983).
Moss, "Vaccinia virus: a tool for research and vaccine development", *Science*, 252(5013):1662-1667 (1991).
Moss, "Vaccinia virus vectors", *Biotechnology*, 20:345-362 (1992).
Moss, "Poxvirus expression vectors", *Curr Top Microbiol Immunol*, 158:25-38 (1992).

Moss, "Poxvirus vectors: cytoplasmic expression of transferred genes", *Curr. Opin. Genet. Dev.*, 3:86-90 (1993).
Murphy, et al., New strategies for preventing graft-versus-host disease' *Curr. Opin. Immunol.*, 11:509-515 (1999).
Nabel, et al., "Recombinant gene expression in vivo within endothelial cells of the arterial wall" *Science*, 244(4910):1342-4(1989).
Needleman and Wunsch, "A general method applicable to the search for similarities in the amino acid sequence of two proteins", *J. Mol. Biol.*, 48:443-453 (1970).
Newmark, et al., "Preparation and properties of adducts of streptokinase and streptokinase-plasmin complex with polyethylene glycol and pluronic Polyol F38", *J. Appl. Biochem.*, 4:185-189 (1982).
Nicolau, et al., "In vivo expression of rat insulin after intravenous administration of the liposome-entrapped gene for rat insulin I", *Proc. Natl. Acad. Sci. USA*, 80(4):1068 (1983).
Oestberg, et al., "Human X (mouse X human) hybridomas stably producing human antibodies" *Hybridoma*, 2:361-367 (1983).
Penix, et al., "Two essential regulatory elements in the human interferon gamma promoter confer activation specific expression in T cells", *J. Exp. Med.* 178:1483-1496 (1993).
Piccini, et al., "Vaccinia: virus, vector, vaccine", *Adv. Virus Res.*, 34:43-64 (1988).
Poirier, et al., "Protective immunity evoked by oral administration of attenuated aroA *Salmonella typhimurium* expressing cloned streptococcal M protein", *J. Exp. Med.* 168:25-32 (1988).
Queen, et al., "Cell-type specific regulation of a kappa immunoglobulin gene by promoter and enhancer elements", *Immunol. Rev.*, 89:49 -68 (1986).
Queen, et al., "Humanized antibody that binds to the interleukin 2 receptor", *Proc. Natl. Acad. Sci. USA*, 86:10029-10033 (1989).
Rooney, et al., "The lymphotoxin-beta receptor is necessary and sufficient for LIGHT-mediated apoptosis of tumor cells", *J. Biol. Chem.*, 275(19):14307-15 (2000).
Rosenfeld, et al., "Adenovirus-mediated transfer of a recombinant alpha 1-antitrypsin gene to the lung epithelium in vivo", Science, 252(5004):431-4 (1991).
Sadoff, et al., "Oral *Salmonella typhimurium* vaccine expressing circumsporozoite protein protects against malaria", *Science*, 240(4850):336-338 (1988).
Samulski, et al., "Targeted integration of adeno-associated virus (AAV) into human chromosome 19", *EMBO J.*, 10(12):3941-50 (1991).
Sanni, et al., "Evolution of aminoacyl-tRNA synthetase quaternary structure and activity: *Saccharomyces cerevisiae* mitochondrial phenylalanyl-tRNA synthetase", *Proc. Natl. Acad. Sci. USA*, 88(19):8387-91 (1991).
Schafer, et al., "Induction of a cellular immune response to a foreign antigen by a recombinant *Listeria monocytogenes* vaccine", *J. Immunol.*, 149:53-59 (1992).
Scheu, et al., "Targeted disruption of LIGHT causes defects in costimulatory T cell activation and reveals cooperation with lymphotoxin beta in mesenteric lymph node genesis", *J. Exp. Med.*, 195:1613-1624 (2002).
Shaikh, et al., "Constitutive expression of LIGHT on T cells leads to lymphocyte activation, inflammation, and tissue destruction", *J. Immunol.*, 167(11):6330-7 (2001).
Sinigaglia, et al., "A malaria T-cell epitope recognized in association with most mouse and human MHC class II molecules", *Nature*, 336(6201):778-780 (1988).
Sloane, et al., "Suicidal tumor proteases", *Nature Biotechnology*, 14:826-7 (1996).
Songsivilai and Lachmann, "Bispecific antibody: a tool for diagnosis and treatment of disease", *Clin. Exp. Immunol.*, 79:315-321 (1990).
Sorge, et al., "Amphotropic retrovirus vector system for human cell gene transfer", *Molec. Cell. Biol.*, 4:1730-1737 (1984).
Soriano, et al., "Targeted and nontargeted liposomes for in vivo transfer to rat liver cells of a plasmid containing the preproinsulin I gene", *Proc. Natl. Acad. Sci. USA*, 80:7128 (1983).
Southwood, et al., "Several common HLA-DR types share largely overlapping peptide binding repertoires", *J. Immunology*, 160:3363-3373 (1998).

Spahn, et al., "Role of lymphotoxin in experimental models of infectious diseases: potential benefits and risks of a therapeutic inhibition of the lymphotoxin-beta receptor pathway", *Infect. Immun.*, 73:7077-7088 (2005).
Stover, et al., "New use of BCG for recombinant vaccines", *Nature*, 351(6326):456-460 (1991).
Sutter, et al., "Nonreplicating vaccinia vector efficiently expresses recombinant genes", *Proc. Natl. Acad. Sci. USA*, 89:10847-10851 (1992).
Tamada, et al., "Cutting edge: selective impairment of CD8+ T cell function in mice lacking the TNF superfamily member LIGHT", *J. Immunol*, 168:4832-4835 (2002).
Tamada, et al., "LIGHT, a TNF-like molecule, costimulates T cell proliferation and is required for dendritic cell-mediated allogeneic T cell response.", *J. Immunol.*, 164(8):4105-10 (2000).
Tamada, et al., "Modulation of T-cell-mediated immunity in tumor and graft-versus-host disease models through the LIGHT co-stimulatory pathway", *Nat. Med.*, 6(3):283-9 (2000).
Tamada, et al., "Blockade of LIGHT/LTbeta and CD40 signaling induces allospecific T cell energy, preventing graft-versus-host disease", *J. Clin. Invest.*, 109:549-557 (2002).
Temin, "Safety considerations in somatic gene therapy of human disease with retrovirus vectors", *Human Gene Therapy*, 1:111-23 (1990).
Thompson, et al., "cis-acting sequences required for inducible interleukin-2 enhancer function bind a novel Ets-related protein, Elf-1" *Mol. Cell. Biol.*, 12:1043-1053 (1992).
Tigges, et al., "Human herpes simplex virus (HSV)-specific CD8+ CTL clones recognize HSV-2-infected fibroblasts after treatment with IFN-gamma or when virion host shutoff functions are disabled", *J. Immunol.*, 156:3901-3910 (1996).
Titomirov, et al., "In vivo electroporation and stable transformation of skin cells of newborn mice by plasmid DNA", *Biochim. Biophys. Acta*, 1088(1):131-4 ((1991).
Todd, et al., "Transcription of the interleukin 4 gene is regulated by multiple promoter elements", *J. Exp. Med.* 177:1663-1674 (1993).
Wang, et al., "pH-sensitive immunoliposomes mediate target-cell-specific delivery and controlled expression of a foreign gene in mouse", *Proc. Natl. Acad. Sci. USA*, 84(22):7851-5 (1987).
Wang, et al., "The regulation of T cell homeostasis and autoimmunity by T cell-derived LIGHT", *J. Clin. Invest.*, 108(12):1771-80 (2001).
Wang, et al., "The critical role of LIGHT in promoting intestinal inflammation and Crohn's disease", *J. Immunol.*, 174(12):8173-82 (2005).
Weiss, "Hot prospect for new gene amplifier", *Science*, 254:1292-1293 (1991).
Williams, et al., "Introduction of foreign genes into tissues of living mice by DNA-coated microprojectiles", *Proc. Natl. Acad. Sci. USA*, 88:2726 (1991).
Wilson, et al., "Hepatocyte-directed gene transfer in vivo leads to transient improvement of hypercholesterolemia in low density lipoprotein receptor-deficient rabbits", *J. Biol. Chem.* 267(2):963-7 (1992).
Wolff, et al., "Direct gene transfer into mouse muscle in vivo", *Science*, 247 (4949 Pt1)-:1465-8 (1990).
Wong, et al., "Human GM-CSF: molecular cloning of the complementary DNA and purification of the natural and recombinant proteins", *Science*, 228(4701):810-815 (1985).
Wu, et al., "Receptor-mediated gene delivery and expression in vivo", *J. Biol. Chem.*, 263:14621-4 (1988).
Wu, et al., "Targeting genes: delivery and persistent expression of a foreign gene driven by mammalian regulatory elements in vivo" *J. Biol. Chem.*, 264(29):16985-7 (1989).
Wu, et al., "The requirement of membrane lymphotoxin for the presence of dendritic cells in lymphoid tissues", *J. Exp. Med.*, 190:629-638 (1999).
Wu, et al., "Signal via lymphotoxin-beta R on bone marrow stromal cells is required for an early checkpoint of NK cell development", *J. Immunol.*, 166:1684-1689 (2001).
Xu, et al., "Critical Role of LIGHT-HVEM interaction in the pathogenesis of GVDH", *J. Immunol.*, 176(Suppl S):S170 (2006).

Xu, et al., "Selective targeting of the LIGHT-HVEM costimulatory system for the treatment of graft-versus-host disease", *Blood*, 109:4097-104 (2007).

Yang, et al., "In vivo and in vitro gene transfer to mammalian somatic cells by particle bombardment", *Proc. Natl. Acad. Sci. USA*, 87:9568-72 (1990).

Yang, "Gene transfer into mammalian somatic cells in vivo", *Crit. Rev. Biotechnol.*, 12:335-356 (1992).

Ye, et al., "Modulation of LIGHT-HVEM costimulation prolongs cardiac allograft survival", *J. Exp. Med.*, 195:795-800 (2002).

Yu, et al., "Priming of naive T cells inside tumors leads to eradication of established tumors", *Nat. Immunol.*, 5(2):141-9 (2004).

Zelenin, et al., "Genetic transformation of mouse cultured cells with the help of high-velocity mechanical DNA injection", *FEBS Lett.*, 244(1):65 -7 (1989).

Zelenin, et al., "High-velocity mechanical DNA transfer of the chloramphenicolacetyl transferase gene into rodent liver, kidney and mammary gland cells in organ explants and in vivo", *FEBS Lett.* 280(1):94-6 (1991).

* cited by examiner

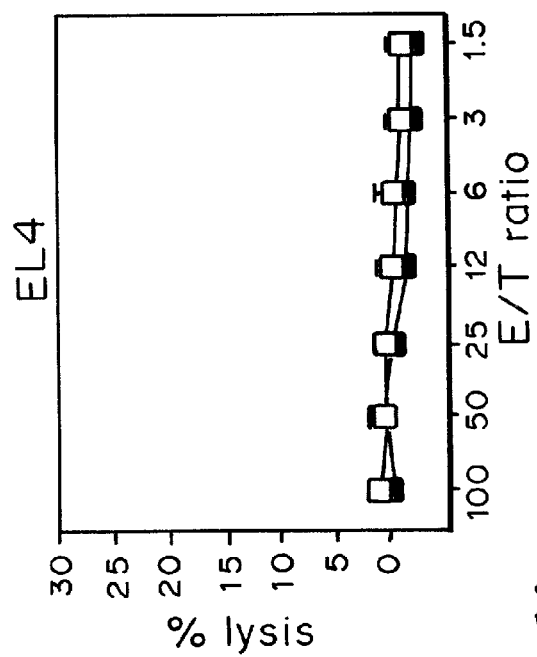
FIG. 1A
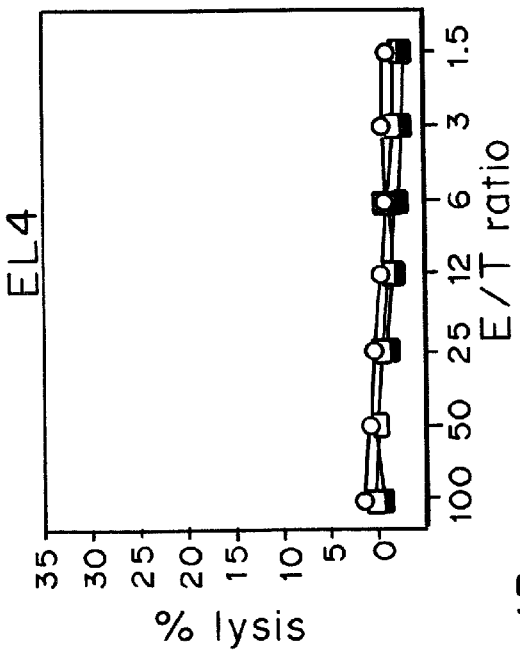
FIG. 1B
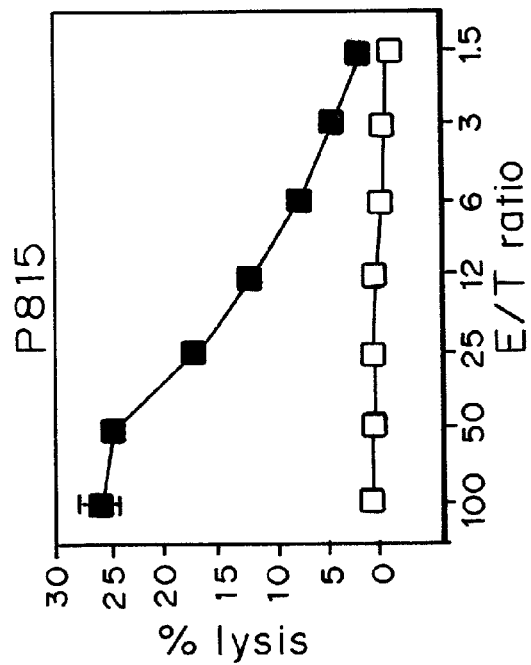
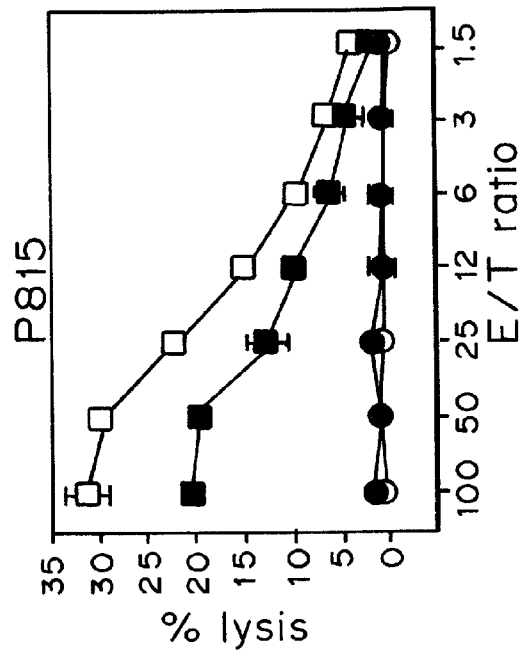

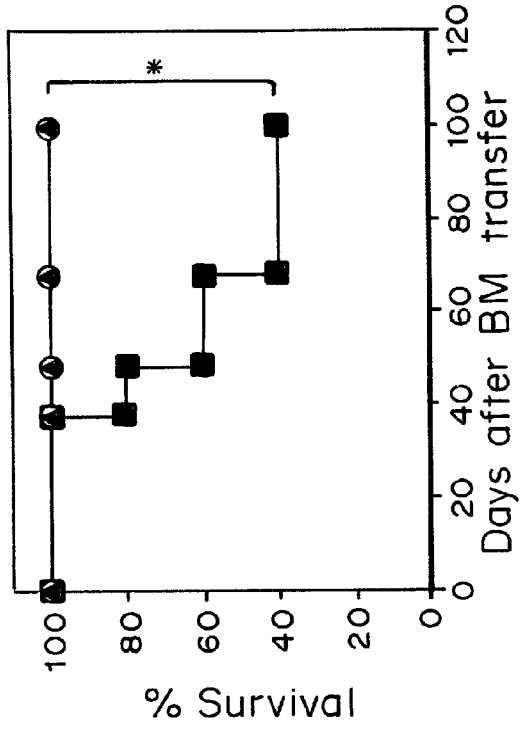
FIG. 1C
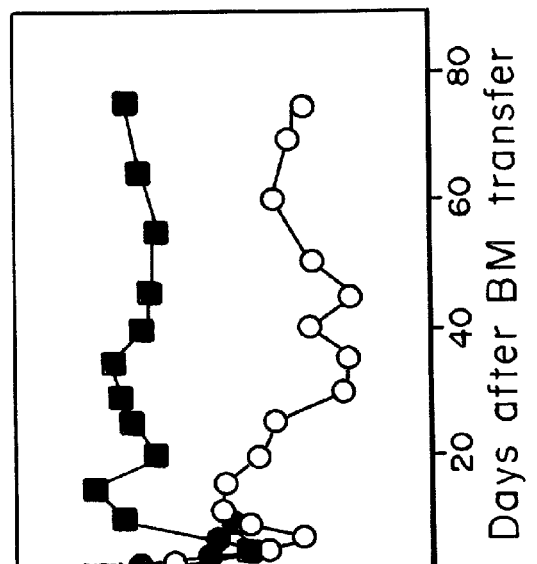
FIG. 1D
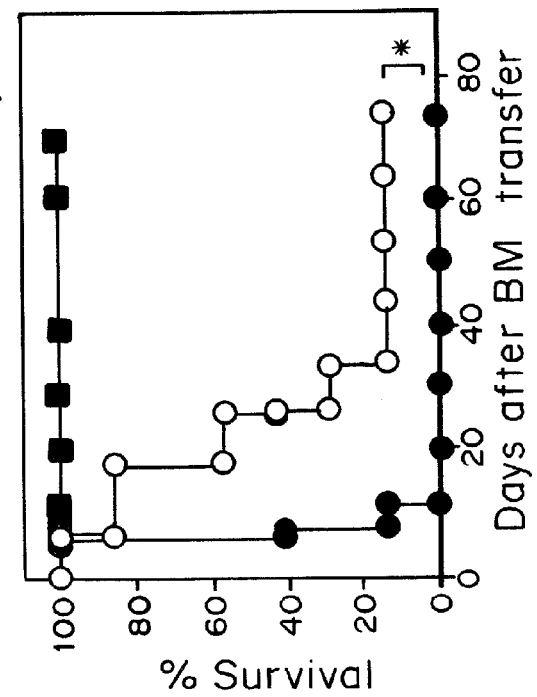

COMPOSITIONS AND METHODS FOR THE TREATMENT OF IMMUNOLOGIC DISORDERS

CROSS-REFERENCE TO RELATED APPLICATIONS

This application claims priority to and benefit of Provisional U.S. Patent Application No. 60/877,176 filed on Dec. 26, 2006.

GOVERNMENT SUPPORT

This invention was made with government support awarded by the National Institutes of Health under Grant Number CA 1085721. The United States government has certain rights in this invention.

FIELD OF THE INVENTION

This invention relates to compositions and methods for reducing inflammatory immune responses, in particular to compositions and methods for treating or inhibiting inflammatory responses related to autoimmune disorders or immune responses related to transplanted cells or tissues including graft-versus-host disease.

BACKGROUND OF THE INVENTION

The functional network of tumor necrosis factor (TNF) and TNF receptor superfamily members is composed of complex cross-talk between multiple ligands and multiple receptors, which regulate pleiotropic functions in the immune system (Aggarwal, *Nat. Rev. Immunol.*, 3(9):745-56 (2003)). LIGHT, standing for homologous to lymphotoxins, exhibits inducible expression, and competes with herpes simplex virus glycoprotein D for herpesvirus entry mediator (HVEM), a receptor expressed by T lymphocytes, is a type II transmembrane glycoprotein belonging to the TNF ligand superfamily (Mauri, et al., *Immunity*, 8(1):21-30 (1998)). LIGHT is expressed on immature dendritic cells (DCs) and activated T cells (Mauri, et al., *Immunity*, 8(1):21-30 (1998); Tamada, et al., *J. Immunol.*, 164(8):4105-10 (2000)) and interacts with two functional receptors: lymphotoxin-β receptor (LTβR) and HVEM (Mauri, et al., *Immunity*, 8(1):21-30 (1998)). LIGHT interaction with LTβR triggers the production of proinflammatory mediators (Lee, et al., *Arterioscler. Thromb. Vasc. Biol.*, 21(12):2004-10 (2001); Kim, et al., *Immunology*, 114(2):272-9 (2005)), up-regulates adhesion molecule expression (Yu, et al., *Nat. Immunol.*, 5(2): 141-9 (2004)), and induces apoptotic cell death in certain tumors (Rooney, et al., *J. Biol. Chem.*, 275(19):14307-15 (2000)). On the other hand, by signaling through HVEM, LIGHT costimulates T-cell activation (Tamada, et al., *Nat. Med.*, 6(3):283-9 (2000)). In vivo experiments demonstrated that transgenic expression of LIGHT leads to spontaneous progression of inflammatory autoimmunity such as Crohn's disease (Wang, et al., *J. Clin. Invest.*, 108(12):1771-80 (2001); Shaikh, et al., *J. Immunol.*, 167(11):6330-7 (2001); Wang, et al., *J. Immunol.*, 174(12):8173-82 (2005)), while genetic disruption of LIGHT results in impaired T-cell activation, particularly in CD8$^+$ T cells (Ye, et al., *J. Exp. Med.*, 195:795-800 (2002); Tamada, et al., *J. Immunol.*, 168:4832-4835 (2002); Scheu, et al., *J. Exp. Med.*, 195:1613-1624 (2002); Liu, et al., *Int. Immunol.*, 15:861-870 (2003)), and renders mice less vulnerable to pathogenic inflammation, as shown in acute hepatitis models (Anand, et al., *J. Clin. Invest*, 116:1045-1051 (2006)). Thus, LIGHT regulates multiple immune functions of innate and adaptive immunity through interactions with LTβR and HVEM.

There are reports demonstrating therapeutic effects of decoy proteins of LTβR in various immunologic diseases, including autoimmunity, inflammation, and transplantation (Gommerman, et al., *Nat. Rev. Immunol.*, 3:642-655 (2003); Spahn, et al., *Infect. Immun.*, 73:7077-7088 (2005)), indicating that decoy LTβR could be a potential biologic for clinical immunotherapy, analogous to a decoy form of TNF-receptor (Moreland, et al., *N. Engl. J. Med.*, 337:141-147 (1997)). Prolonged administration of decoy LTβR, however, might become a double-edged sword since it abrogates the maintenance of DC and natural killer/natural killer T (NK/NKT) cells (Wu, et al., *J. Exp. Med.*, 190:629-638 (1999); Iizuka, et al., *Proc. Natl. Acad. Sci. U.S.A.*, 96:6336-6340 (1999)) and inhibits the microstructure formation of lymphoid organs (Mackay, et al., *Eur. J. Immunol.*, 27:2033-2042 (1997)), thus disrupting immune homeostasis.

Graft-versus-host disease (GVHD) is a major complication associated with allogeneic hematopoietic stem cell transplantation. Posttransplantation administration of immunosuppressants prevails as the current therapeutic choice for GVHD, but this treatment results in systemic immunosuppression that often leads to opportunistic pathogen infections and leukemic relapse (Murphy, et al, *Curr. Opin. Immunol.*, 11:509-515 (1999); Blazar, et al., *Philos. Trans. R. Soc. Lond. B Biol. Sci.*, 360:1747-1767 (2005)). To overcome these issues, blockade of T-cell costimulatory signals is among the most sought after alternatives to immunosuppressants (Murphy, et al., *Curr. Opin. Immunol.*, 11:509-515 (1999); Blazar, et al., *Philos. Trans. R. Soc. Lond. B Biol. Sci.*, 360:1747-1767 (2005)). Previous findings have suggested a therapeutic potential of LIGHT costimulation, in which administration of LTβR-Ig, a decoy LTβR, inhibits alloreactive cytotoxic T lymphocyte (CTL) generation and prolongs the survival of GVHD mice (Tamada, et al., *Nat. Med.*, 6:283-289 (2000)). Combined therapy of LTβR-Ig and anti-CD40 ligand monoclonal antibody (mAb) further protects the recipient mice from GVHD by rendering alloreactive donor CTL anergic (Tamada, et al., *J. Clin. Invest.*, 109:549-557 (2002)). However, the actual contribution of the LIGHT-HVEM costimulatory system to these findings remains elusive due to the antihomeostatic effects of decoy LTβR. It is possible that changes of DC function or cellular structure in lymphoid tissues could affect the intensity of adaptive immune responses. Direct evidence indicating a pathogenic role of LIGHT-HVEM costimulation in GVHD has not been elucidated.

It would be advantageous to provide new compositions and methods for separating the therapeutic effects of decoy LTβR from the potential adverse effects. While decoy LTβR interferes with three molecular interactions—LTβ-LTβR, LIGHT-LTβR, and LIGHT-HVEM—the antihomeostatic effects are largely dependent on LTβ-LTβR functions since the corresponding phenotypes are observed in LTβ- or LTβR-KO mice but not in LIGHT-KO mice (Ye, et al., *J. Exp. Med.*, 195:795-800 (2002); Tamada, et al., *J. Immunol.*, 168:4832-4835 (2002); Scheu, et al., *J. Exp. Med.*, 195:1613-1624 (2002); Liu, et al., *Int. Immunol.*, 15:861-870 (2003); Kabashima, et al., *Immunity*, 22:439-450 (2005); Wu, et al., *J. Immunol.*, 166:1684-1689 (2001); Alimzhanov, et al., *Proc. Natl. Acad. Sci. U.S.A.*, 94:9302-9307 (1997); Futterer, et al., *Immunity*, 9:59-70 (1998)).

Therefore, it is an object of the invention to provide compositions and methods of use thereof that reduce inflammatory immune responses but do not significantly disrupt normal immune system homeostasis such as by interfering with the maintenance of DC and natural killer/natural killer T (NK/NKT) cells or by inhibiting the microstructure formation of lymphoid organs.

It is another object of the invention to provide compositions and methods of use thereof that inhibit or reduce T cell costimulatory signals.

It is another object of the invention to provide compositions and methods for the treatment of immunologic disorders, including inflammatory responses.

It is another object of the invention to provide compositions and methods for the treatment of autoimmune disorders.

It is still another object of the invention to provide compositions and methods for treatment of graft rejection and graft-versus-host disease.

SUMMARY OF THE INVENTION

Compositions and methods for preventing, reducing or inhibiting immunologic disorders are provided herein. Suitable compositions include one or more LIGHT-HVEM antagonists. LIGHT-HVEM antagonists include compounds that inhibit, reduce, or block the biological activity or expression of LIGHT and/or HVEM.

LIGHT-HVEM antagonists can reduce or inhibit the binding of LIGHT to HVEM, but do not significantly modulate the binding of LTβ to LTβR. Exemplary LIGHT-HVEM antagonists that reduce or inhibit the binding of LIGHT to HVEM include antibodies and antigen-binding antibody fragments, decoy polypeptides and small molecule inhibitors. LIGHT-HVEM antagonists that are capable of binding to LIGHT or HVEM do not increase LIGHT or HVEM activity in a cell expressing LIGHT or HVEM on its surface. In some embodiments LIGHT-HVEM antagonists are capable of reducing or inhibiting one or more activities of LIGHT or HVEM in a cell expressing LIGHT or HVEM on its surface. In some embodiments, the cell is a lymphocyte, a T cell, a CD4+ T cell, a CD8+ T cell, a $T_h1$ cell, a B cell, a plasma cell, a macrophage, or an NK cell. In preferred embodiments, the cell is a T cell.

LIGHT-HVEM antagonistic antibodies bind to LIGHT or HVEM and reduce or inhibit the binding of LIGHT to HVEM. In preferred embodiments, LIGHT-HVEM antagonistic antibodies specifically bind to an extracellular portion of LIGHT or HVEM. LIGHT-HVEM antagonistic antibodies can be monoclonal or polyclonal, antiidiotypic, xenogeneic, allogeneic, syngeneic, or modified forms thereof, such as humanized or chimeric antibodies. The antibodies can also be antibody fragments or single chain antibodies. An exemplary antibody is mAb LBH1.

Polypeptides that bind to LIGHT or HVEM and inhibit or reduce binding between LIGHT and HVEM are also provided. Suitable polypeptides include fragments of LIGHT or HVEM. In preferred embodiments, the polypeptides are soluble fragments of LIGHT or HVEM. Exemplary soluble fragments of LIGHT and HVEM include the extracellular domains of LIGHT or HVEM or fragments thereof. Other suitable polypeptides include soluble fragments or receptors of HVEM that are not LIGHT and soluble fragments or receptors of LIGHT that are not HVEM. Exemplary of these polypeptides are lymphotoxin-α, herpesvirus gD protein and the TR6 receptor. Polypeptide LIGHT-HVEM antagonists may contain one or more substitutions, deletions or insertions of amino acids relative to their wild-type sequence, and may be in the form of fusion proteins.

LIGHT-HVEM antagonists that reduce or inhibit the expression of LIGHT or HVEM are also provided. Suitable LIGHT-HVEM antagonists include inhibitory nucleic acids, including, but not limited to, ribozymes, triplex-forming oligonucleotides (TFOs), antisense DNA, siRNA, and microRNA specific for nucleic acids encoding LIGHT or HVEM.

Methods for using LIGHT-HVEM antagonists to reduce or inhibit T cell activation and survival are also provided. Therapeutic uses for LIGHT-HVEM antagonists are provided. LIGHT-HVEM antagonists can be used to prevent or treat immunologic diseases and disorders including graft rejection, graft-versus-host disease, inflammatory immune responses, and autoimmune disorders.

BRIEF DESCRIPTION OF THE DRAWINGS

FIG. 1A is a series of line graphs showing anti-host cytotoxic T lymphocyte (CTL) activity of spleen cells isolated from recipient BDF1 ($H-2^d$) mice intravenously injected with either wild-type (WT) or LIGHT-KO B6 ($H-2^b$) spleen cells. CTL activity was measured against P815 ($H-2^d$) and EL4 ($H-2^b$) tumor cells by $^{51}$Cr-release assay. Data are expressed as percent lysis as a function of effector cell/target cell ratio. The closed squares represent data obtained using spleen cells from BDF1 mice injected with spleen cells from WT B6 mice and the open squares represent data obtained using spleen cells from BDF1 mice injected with spleen cells from LIGHT-KO B6 mice.

FIG. 1B is a series of line graphs showing anti-host cytotoxic T lymphocyte (CTL) activity of spleen cells isolated from recipient BDF1 ($H-2^d$) mice intravenously injected with various combinations of T cells and non-T cells from either wild-type (WT) or LIGHT-KO B6 ($H-2^b$) mice. CTL activity was measured against P815 ($H-2^d$) and EL4 ($H-2^b$) tumor cells by $^{51}$Cr-release assay. Data are expressed as percent lysis as a function of effector cell/target cell ratio. T cells and non-T cells purified from spleen cells of WT or LIGHT-KO B6 mice were injected in BDF1 mice in the following combinations: WT T cells plus WT non-T cells (open squares), WT T cells plus LIGHT-KO non-T cells (closed squares), LIGHT-KO T cells plus WT non-T cells (open circles), and LIGHT-KO T cells plus LIGHT-KO non-T cells (closed circles).

FIG. 1C is a line graph showing survival of BDF1 mice subjected to lethal-dose irradiation (12 Gy) followed by intravenous injection of T cell-depleted B6 BM cells alone (open circles) or together with WT (closed squares) or LIGHT-KO (closed triangles) B6 T cells. Data are expressed as percent survival as a function of time in days.

FIG. 1D is a series of line graphs showing survival and body weight changes of BALB/c mice subjected to lethal-dose irradiation (10 Gy) followed by intravenous injection of T cell-depleted B6 BM cells alone (closed squares) or together with WT (closed circles) or LIGHT-KO (open circles) B6 T cells. Data are expressed as percent survival or percent body weight as a function of time in days.

DETAILED DESCRIPTION OF THE INVENTION

I. Definitions

Figure 2:
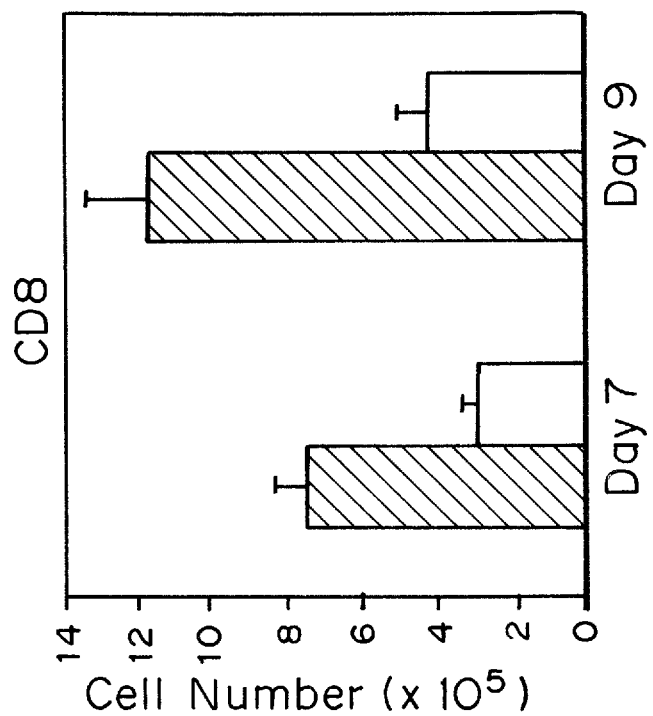
FIG. 2 is a series of bar graphs showing absolute numbers of WT (closed bars) or LIGHT-KO (open bars) B6 donor CD4$^+$ or CD8$^+$ T cells in total spleen or liver lymphocytes from recipient BDF1 mice. Data are expressed as total cell number ($\times 10^6$).
Figure 2:
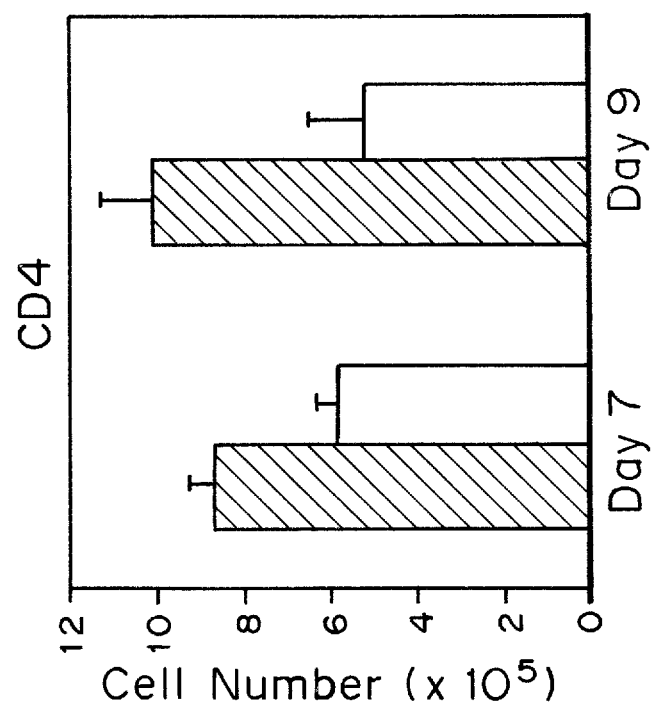

Terms defined herein have meanings as commonly understood by a person of ordinary skill in the art Terms such as "a", "an" and "the" are not intended to refer to only a singular entity, but include the general class of which a specific example may be used for illustration.

As used herein, the term "LIGHT-HVEM antagonist" refers to compounds that inhibit, reduce, or block the biological activity or expression of LIGHT and/or HVEM. LIGHT-HVEM antagonists disclosed herein do not significantly modulate the binding of LTβ to LTβR. Suitable LIGHT-HVEM antagonists include, but are not limited to, antibodies and antibody fragments that bind HVEM or LIGHT, LIGHT or HVEM decoy polypeptides including soluble fragments of LIGHT or HVEM, small organic compounds, and inhibitory nucleic acids specific for LIGHT- or HVEM-encoding nucleic acids.

As used herein the term "isolated" is meant to describe a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

As used herein, the term "polypeptide" refers to a chain of amino acids of any length, regardless of modification (e.g., phosphorylation or glycosylation).

As used herein, a "variant" polypeptide contains at least one amino acid sequence alteration (addition, deletion, substitution, preferably conservative i.e., not substantially changing the function except in magnitude) as compared to the amino acid sequence of the corresponding wild-type polypeptide.

As used herein, an "amino acid sequence alteration" can be, for example, a substitution, a deletion, or an insertion of one or more amino acids.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences As used herein, an "expression control sequence" is a DNA sequence that controls and regulates the transcription and/or translation of another DNA sequence.

As used herein, "operably linked" means incorporated into a genetic construct so that expression control sequences effectively control expression of a coding sequence of interest.

As used herein, a "fragment" of a polypeptide refers to any subset of the polypeptide that is a shorter polypeptide of the full length protein. Generally, fragments will be five or more amino acids in length.

As used herein, "conservative" amino acid substitutions are substitutions wherein the substituted amino acid has similar structural or chemical properties.

As used herein, "non-conservative" amino acid substitutions are those in which the charge, hydrophobicity, or bulk of the substituted amino acid is significantly altered.

As used herein, "isolated nucleic acid" refers to a nucleic acid that is separated from other nucleic acid molecules that are present in a mammalian genome, including nucleic acids that normally flank one or both sides of the nucleic acid in a mammalian genome.

As used herein with respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "host cell" refers to prokaryotic and eukaryotic cells into which a recombinant expression vector can be introduced.

As used herein, "transformed" and "transfected" encompass the introduction of a nucleic acid (e.g. a vector) into a cell by a number of techniques known in the art.

The terms "individual", "host", "subject", and "patient" are used interchangeably herein.

As used herein the term "effective amount" or "therapeutically effective amount" means a dosage sufficient to treat, inhibit, or alleviate one or more symptoms of an inflammatory response or autoimmune disease state being treated or to otherwise provide a desired pharmacologic and/or physiologic effect. The precise dosage will vary according to a variety of factors such as subject-dependent variables (e.g., age, immune system health, etc.), the disease, and the treatment being effected.

As used herein, the phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$, or $10^{10}$ $M^{-1}$. Affinities greater than $10^8$ $M^{-1}$ are preferred.

As used herein, the terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

As used herein, an "antigen" is an entity to which an antibody specifically binds.

As used herein, the terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids, in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. 156, 3901-3910) or by cytokine secretion.

As used herein, the terms "immunologic", "immunological" or "immune" response is the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

II. Compositions

A. LIGHT-HVEM Antagonists

It has been discovered that LIGHT and HVEM promote T cell activation and survival during immunologic responses. It is believed that LIGHT-HVEM binding on T cells is the mechanism for promoting activation and survival. Compositions including on or more LIGHT-HVEM antagonists are provided herein. LIGHT-HVEM antagonists include compounds that inhibit, reduce, or block the biological activity or expression of LIGHT and/or HVEM.

In certain embodiments, the compositions include as an active agent one or more LIGHT-HVEM antagonists in an amount effective to inhibit, reduce, or decrease an immunologic response.

Human LIGHT is expressed as at least two isoforms produced through alternative splicing of LIGHT mRNA. The amino acid sequences of human LIGHT isoforms are known in the art and are provided at GENBANK accession numbers NP_003798 (isoform1) and NP_742011 (isoform 2). The nucleic acid sequence of human LIGHT isoform mRNAs are known in the art and are provided at GENBANK accession numbers NM_003807 (isoform 1) and NM_172014 (isoform 2). The coding region of the LIGHT mRNA provided by accession number NM_172014 is from nucleotides 383-997. The coding region of the LIGHT mRNA provided by accession number NM_003807 is from nucleotides 383-1105.

The amino acid sequence of human HVEM is known in the art and is provided at GENBANK accession number AAQ89238. Full length human HVEM is 283 amino acids in length. The nucleic acid sequence of human HVEM mRNA is known in the art and is provided at GENBANK accession number AY358879. The coding region of the HVEM mRNA is from nucleotides 82 to 933 of accession number AY358879.

Both LIGHT and HVEM are expressed as transmembrane proteins, each with an intracellular domain, a single membrane-spanning domain, and an extracellular domain. The extracellular domain of human LIGHT includes from about amino acid 60 to amino acid 240 of GENBANK accession number NP_003798 and from about amino acid to amino acid of GENBANK accession number NP_742011 (NP_742011 variant lacks transmembrane region and probably soluble protein). The extracellular domain of human HVEM includes from about amino acid 1 to amino acid 202 of GENBANK accession number AAQ89238.

The extracellular domain of LIGHT includes β-strand scaffold forming an anti-parallel β-sandwich structure and assembling a trimer. Extracellular domain of LIGHT has a single potential site of N-linked glycan. The extracellular domain of HVEM includes four cysteine-rich repeats and two potential sites of N-linked glycans. HVEM binds with LIGHT through second and third cysteine-rich domains.

1. LIGHT-HVEM Antagonists that Reduce or Inhibit the Binding of LIGHT to HVEM

LIGHT-HVEM antagonists that reduce or inhibit the binding of LIGHT to HVEM do not significantly modulate the binding of LTβ to LTβR. In preferred embodiments LIGHT-HVEM antagonists reduce the binding of LTβ to LTβR by less than 50%, 40%, 30%, 20%, 10%, 5% or less, as compared to controls. LIGHT-HVEM antagonists can be competitive or non-competitive inhibitors of LIGHT-HVEM binding. LIGHT-HVEM antagonists that reduce or inhibit the binding of LIGHT to HVEM include antibodies and antibody fragments that bind HVEM or LIGHT, LIGHT or HVEM decoy polypeptides including soluble fragments of LIGHT or HVEM, and small organic compounds.

LIGHT-HVEM antagonists that bind to LIGHT or HVEM reduce or inhibit the interaction between LIGHT and HVEM by at least 20%, more preferably by at least 30%, more preferably by at least 40%, 50%, 60%, 70%, 80%, 90%, 95%, 96%, 97%, 98%, 99% or more.

LIGHT-HVEM antagonists that are capable of binding to LIGHT or HVEM do not increase LIGHT or HVEM activity in a cell expressing LIGHT or HVEM on its surface. In some embodiments LIGHT-HVEM antagonists are capable of reducing or inhibiting one or more activities of LIGHT or HVEM in a cell expressing LIGHT or HVEM on its surface. In some embodiments, the cell is a lymphocyte, a T cell, a CD4+ T cell, a CD8+ T cell, a $T_h1$ cell, a B cell, a plasma cell, a macrophage, or an NK cell. In preferred embodiments, the cell is a T cell. LIGHT-HVEM antagonists that bind to LIGHT or HVEM reduce or inhibit one or more LIGHT or HVEM activities by at least 20%, more preferably by at least 30%, more preferably by at least 40%, 50%, 60%, 70%, 80%, 90%, 95%, 96%, 97%, 98%, 99% or more.

a. Antibodies

In one embodiment, LIGHT-HVEM antagonists are antibodies. Antibodies or antibody fragments that specifically bind to LIGHT or HVEM can be used to reduce or inhibit the binding of LIGHT to HVEM. Methods of producing antibodies are well known and within the ability of one of ordinary skill in the art and are described in more detail below.

The antibodies disclosed herein specifically bind to a LIGHT or an HVEM protein and are capable of reducing or inhibiting the binding of LIGHT to HVEM. These antibodies are defined as "blocking", "function-blocking" or "antagonistic" antibodies. In preferred embodiments the antagonistic antibodies specifically bind to a portion of the extracellular domain of LIGHT or HVEM. In other embodiments, the antagonistic antibodies specifically bind to the β-strand scaffold domain of LIGHT or the cysteine-rich repeats domain of HVEM.

The immunogen used to generate the antibody may be any immunogenic portion of LIGHT or HVEM. Preferred immunogens include all or a part of the extracellular domain of human LIGHT or HVEM, where these residues contain the post-translation modifications, such as glycosylation, found on native LIGHT or HVEM. In other embodiments the immunogen may be the β-strand scaffold domain of LIGHT or the cysteine-rich repeats domain of HVEM. Immunogens including the extracellular domain or immunogenic fragments thereof are produced in a variety of ways known in the art, e.g., expression of cloned genes using conventional recombinant methods, synthesized peptide complexes, isolation from cells of origin, cell populations expressing high levels of LIGHT or HVEM.

The antibodies disclosed herein are capable of binding to a polypeptide having at least about 70%, more preferably 75%, 80%, 85%, 90%, 95% identity to human LIGHT, as found at GENBANK accession numbers NP_003798 (isoform1) and NP_742011 (isoform 2), or HVEM, as found at GENBANK accession number AAQ89238.

The antibodies may be polyclonal or monoclonal antibodies. The antibodies may be xenogeneic, allogeneic, syngeneic, or modified forms thereof such as humanized or chimeric antibodies. The antibodies may also be antiidiotypic antibodies. Antibodies, as used herein, also includes antibody fragments including Fab and F(ab)$_2$ fragments, and antibodies produced as a single chain antibody or scFv instead of the normal multimeric structure. The antibodies may be an IgG such as IgG1, IgG2, IgG3 or IgG4; or IgM, IgA, IgE or IgD isotype. The constant domain of the antibody heavy chain maybe selected depending on the effector function desired. The light chain constant domain may be a kappa or lambda constant domain.

Exemplary antibodies against mouse HVEM are mAbs LBH1 (Xu, et al., *Blood,* 109:4097-104 (2007)) and LH1 (Anand, et al. *J. Clin. Invest.,* 116:1045-1051 (2006)). Exemplary antibodies against mouse LIGHT are ML69 and ML209 (Tamada, et al. *Nat. Med.,* 6:283-289 (2000)).

Hybridoma cell line LBH1 was deposited by The Johns Hopkins Technology Transfer Office on Oct. 18, 2011 under the terms of the Budapest Treaty on the International Recognition of the Deposit of Microorganisms for the purposes of Patent Procedure with the American Type Culture Collection ("ATCC"), Manassas, Va., United States, Patent Deposit Designation PTA-12171.

b. Polypeptides

In another embodiment, LIGHT-HVEM antagonists are polypeptides that bind to LIGHT or HVEM. LIGHT- or HVEM-binding polypeptides can be used to reduce or inhibit the binding of LIGHT to HVEM. LIGHT-HVEM antagonist polypeptides are also referred to herein as "decoy polypeptides". Methods of producing polypeptides are well known and within the ability of one of ordinary skill in the art and are described in more detail below.

In some embodiments the polypeptides are soluble fragments of full length LIGHT or HVEM polypeptides. As used herein, a fragment of LIGHT or HVEM refers to any subset of the polypeptide that is a shorter polypeptide of the full length protein. Soluble fragments generally lack some or all of the intracellular and/or transmembrane domains. In some embodiments, soluble fragments of LIGHT or HVEM include the entire extracellular domains of these proteins. In other embodiments, the soluble fragments of LIGHT or HVEM include fragments of the extracellular domains of these proteins. In other embodiments, useful soluble fragments of LIGHT include the β-strand scaffold domain and useful soluble fragments of HVEM include the cysteine-rich repeats domain.

In another embodiment, the polypeptides are soluble fragments of receptors of HVEM other than LIGHT or soluble fragments of receptors of LIGHT other than HVEM. As discussed above, LIGHT-HVEM antagonists disclosed herein do not significantly modulate the binding of LTβ to LTβR. Therefore polypeptide fragments of LTβ or LTβR are specifically excluded from the compositions and methods disclosed herein.

Additional receptors for HEVM include lymphotoxin-α (GENBANK accession number AY070490) and hepesvirus gD protein (GENBANK accession number L09242). An additional receptor for LIGHT is the TR6 receptor (GENBANK accession number AF134240).

The polypeptide LIGHT-HVEM antagonists can be derived from any species of origin. In a preferred embodiment the polypeptide LIGHT-HVEM antagonists are of human origin.

The polypeptides disclosed herein include variant polypeptides. As used herein, a "variant" polypeptide contains at least one amino acid sequence alteration as compared to the amino acid sequence of the corresponding wild-type polypeptide. An amino acid sequence alteration can be, for example, a substitution, a deletion, or an insertion of one or more amino acids.

A variant LIGHT-HVEM antagonistic polypeptide can have any combination of amino acid substitutions, deletions or insertions. In one embodiment, isolated LIGHT-HVEM antagonistic variant polypeptides have an integer number of amino acid alterations such that their amino acid sequence shares at least 60, 70, 80, 85, 90, 95, 97, 98, 99, 99.5 or 100% identity with an amino acid sequence of a corresponding wild type amino acid sequence. In a preferred embodiment, LIGHT-HVEM antagonistic variant polypeptides have an amino acid sequence sharing at least 60, 70, 80, 85, 90, 95, 97, 98, 99, 99.5 or 100% identity with the amino acid sequence of a corresponding wild type polypeptide.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch (*J. Mol. Biol.,* 48:443-453 (1970)); 2) BLOSSUM62 comparison matrix from Hentikoff and Hentikoff (*Proc. Natl. Acad. Sci. U.S.A.,* 89:10915-10919 (1992)) 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)*100. For this calculation, alignment length includes internal gaps but does not include terminal gaps.

Amino acid substitutions in LIGHT-HVEM antagonistic variant polypeptides may be "conservative" or "non-conservative". As used herein, "conservative" amino acid substitutions are substitutions wherein the substituted amino acid has similar structural or chemical properties, and "non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain.

Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glu, Gln); polar, positively charged residues (His, Arg, Lys); large aliphatic, nonpolar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

LIGHT-HVEM antagonistic variant polypeptides may be modified by chemical moieties that may be present in polypeptides in a normal cellular environment, for example, phosphorylation, methylation, amidation, sulfation, acylation, glycosylation, sumoylation and ubiquitylation. LIGHT-HVEM antagonistic variant polypeptides may also be modified with a label capable of providing a detectable signal, either directly or indirectly, including, but not limited to, radioisotopes and fluorescent compounds.

LIGHT-HVEM antagonistic variant polypeptides may also be modified by chemical moieties that are not normally added to polypeptides in a cellular environment. Such modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N═C═N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues can be converted to asparaginyl and glutaminyl residues by reaction with ammonia. Polypeptides may also include one or more D-amino acids that are substituted for one or more L-amino acids.

The LIGHT-HVEM antagonistic variant polypeptides disclosed herein may be coupled to other polypeptides to form fusion proteins. Provided are LIGHT-HVEM antagonistic variant polypeptides having a first fusion partner comprising all or a part of a LIGHT-HVEM antagonistic variant polypeptide fused (i) directly to a second polypeptide or, (ii) optionally, fused to a linker peptide sequence that is fused to the second polypeptide. The presence of the fusion partner can alter the solubility, affinity and/or valency of the LIGHT-HVEM antagonistic variant polypeptide. As used herein, "valency" refers to the number of binding sites available per molecule. LIGHT-HVEM antagonistic variant fusion proteins described herein include any combination of amino acid alteration (i.e. substitution, deletion or insertion), fragment, and/or modification as described above.

The second polypeptide binding partner may be N-terminal or C-terminal relative to the LIGHT-HVEM antagonistic variant polypeptide. In a preferred embodiment, the second polypeptide is C-terminal to the LIGHT-HVEM antagonistic variant polypeptide.

A large number of polypeptide sequences that are routinely used as fusion protein binding partners are well known in the art. Examples of useful polypeptide binding partners include, but are not limited to, green fluorescent protein (GFP), glutathione S-transferase (GST), polyhistidine, myc, hemagglutinin, Flag™ tag (Kodak, New Haven, Conn.), maltose E binding protein, protein A, and one or more domains of an Ig heavy chain constant region, preferably having an amino acid sequence corresponding to the hinge, $C_{H2}$ and $C_{H3}$ regions of a human immunoglobulin Cγ1 chain.

c. Small Molecules and Other Antagonists

It will be appreciated that additional bioactive agents may be screened for LIGHT-HVEM antagonistic activity. In one embodiment, candidate bioactive agents are screened for their ability to reduce binding of LIGHT to HVEM. In another embodiment, candidate bioactive agents are screened for their ability to reduce activation of either LIGHT or HVEM. The assays preferably utilize human LIGHT and human HVEM proteins, although other LIGHT and HVEM proteins may also be used.

The term "candidate bioactive agent" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to bind LIGHT or HVEM may be used.

Candidate agents encompass numerous chemical classes, though typically they are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides, e.g., peptidomimetics. Peptidomimetics can be made as described, e.g., in WO 98156401.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs. In a preferred embodiment, the candidate bioactive agents are organic chemical moieties or small molecule chemical compositions, a wide variety of which are available in the art d. Methods for Measuring LIGHT-HVEM Binding and Activity Methods for measuring binding affinity of between two molecules, such as LIGHT for HVEM, are well known in the art, and include, but are not limited to, fluorescence activated cell sorting (FACS), surface plasmon resonance, fluorescence anisotropy, affinity chromatography and affinity selection-mass spectrometry.

Activities of LIGHT or HVEM that can be measured include T cell survival, T cell activation, and activation of various transcriptional factors including nuclear factor-κB (NF-κB), Jun N-terminal kinase (JNK), and the Jun-containing transcription factor AP-1, through interactions with TNF receptor-associated factor (TRAF)-1, 2, 3, 5, and 6. T cell activation can be measured as an increase in proliferation or secretion of cytokines, including, but not limited to, IL-2. Methods for measuring cell survival, cell proliferation, protein phosphorylation activation of various transcriptional factors including NF-κB, JNK, and AP-1, and cytokine secretion are well known to those of skill in the art.

2. LIGHT-HVEM Antagonists that Reduce or Inhibit the Expression of LIGHT or HVEM In another embodiment LIGHT-HVEM antagonists reduce or inhibit the expression of LIGHT or HVEM. LIGHT-HVEM antagonists that reduce or inhibit expression of LIGHT or HVEM include inhibitory nucleic acids, including, but not limited to, ribozymes, triplex-forming oligonucleotides (TFOs), antisense DNA, siRNA, and microRNA specific for nucleic acids encoding LIGHT or HVEM.

Useful inhibitory nucleic acids include those that reduce the expression of RNA encoding LIGHT or HVEM by at least 20%, 30%, 40%, 50%, 60%, 70%, 80%, 90% or 95% compared to controls. Expression of LIGHT or HVEM can be measured by methods well know to those of skill in the art, including northern blotting and quantitative polymerase chain reaction (PCR).

Inhibitory nucleic acids and methods of producing them are well known in the art. siRNA design software is available for example at http://i.cs.hku.hk/~sirna/software/sirna.php. Synthesis of nucleic acids is well known see for example Molecular Cloning: A Laboratory Manual (Sambrook and Russel eds. 3$^{rd}$ ed.) Cold Spring Harbor, N.Y. (2001). The term "siRNA" means a small interfering RNA that is a short-length double-stranded RNA that is not toxic. Generally, there is no particular limitation in the length of siRNA as long as it does not show toxicity. "siRNAs" can be, for example, 15 to 49 bp, preferably 15 to 35 bp, and more preferably 21 to 30 bp long. Alternatively, the double-stranded RNA portion of a final transcription product of siRNA to be expressed can be, for example, 15 to 49 bp, preferably 15 to 35 bp, and more preferably 21 to 30 bp long. The double-stranded RNA portions of siRNAs in which two RNA strands pair up are not limited to the completely paired ones, and may contain non-pairing portions due to mismatch (the corresponding nucleotides are not complementary), bulge (lacking in the corresponding complementary nucleotide on one strand), and the like. Nonpairing portions can be contained to the extent that they do not interfere with siRNA formation. The "bulge" used herein preferably comprise 1 to 2 nonpairing nucleotides, and the double-stranded RNA region of siRNAs in which two RNA strands pair up contains preferably 1 to 7, more preferably 1 to 5 bulges. In addition, the "mismatch" used herein is contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, the double-stranded RNA region of siRNAs in which two RNA strands pair up may contain both bulge and mismatched, which sum up to, preferably 1 to 7, more preferably 1 to 5 in number.

The terminal structure of siRNA may be either blunt or cohesive (overhanging) as long as siRNA can silence, reduce, or inhibit the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the siRNA is not necessarily the cut off structure at both ends as described above, and may have a stem-loop structure in which ends of one side of double-stranded RNA are connected by a linker RNA. The length of the double-stranded RNA region (stem-loop portion) can be, for example, 15 to 49 bp, preferably 15 to 35 bp, and more preferably 21 to 30 bp long. Alternatively, the length of the double-stranded RNA region that is a final transcription product of siRNAs to be expressed is, for example, 15 to 49 bp, preferably 15 to 35 bp, and more preferably 21 to 30 bp long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA or viral RNA, or an artificial RNA molecule.

MiRNAs are produced by the cleavage of short stem-loop precursors by Dicer-like enzymes; whereas, siRNAs are produced by the cleavage of long double-stranded RNA molecules. MiRNAs are single-stranded, whereas siRNAs are double-stranded.

Methods for producing siRNA are known in the art. Because the sequence for B7-H4 is known, one of skill in the art could readily produce siRNAs that downregulate B7-H4 expression in host using the information that is publicly available.

B. Additional Immunoregulatory Compounds

In certain embodiments, the LIGHT-HVEM antagonists disclosed herein, including antagonistic LIGHT and HVEM antibodies, may be combined with one or more additional therapeutic agents.

The one or more additional therapeutic agents can include agents that modulate the activation state of immune system. These agents are referred to herein as "immunomodulatory" or "immunoregulatory" agents. In one embodiment, the LIGHT-HVEM antagonists described herein can be administered in combination with immunosuppressive agents, e.g., antibodies against other lymphocyte surface markers (e.g., CD40) or against cytokines, other fusion proteins, e.g., CTLA4Ig, or other immunosuppressive drugs (e.g., cyclosporin A, FK506-like compounds, rapamycin compounds, or steroids).

LIGHT-HVEM antagonists may be combined with immunotherapies based on modulation of other negative costimulatory pathways, and with CTLA-4 modulation in particular. For example, LIGHT-HVEM antagonists may be advantageously combined with CTLA-4 mimicking agents such as CTLA-4Ig, which has already found clinical use as an immunosuppressive agent.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO 95122972, WO 95116691, WO 95104738, U.S. Pat. Nos. 6,015,809; 5,989,591; 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. Preferably, the language "rapamycin compound" as used herein does not include FK506-like compounds.

C. Pharmaceutical Compositions

Pharmaceutical compositions including LIGHT-HVEM antagonists, and vectors containing the same are provided. The pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration.

1. Formulations for Parenteral Administration

In a preferred embodiment, the peptides are administered in an aqueous solution, by parenteral injection. The formulation may also be in the form of a suspension or emulsion. In general, pharmaceutical compositions are provided including effective amounts of a LIGHT-HVEM antagonist, or derivative products, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN 20, TWEEN 80, Polysorbate 80), antioxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Enteral Administration

LIGHT-HVEM antagonists can be formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The polypeptide antagonists may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The LIGHT-HVEM antagonists can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e. the drug is enclosed in a semipermeable membrane which allows water to enter and push drug out through a single small opening due to osmotic effects. For oral formulations, the location of release may be the stomach, the small intestine (the duodenum, the jejunem, or the ileum), or the large intestine. Preferably, the release will avoid the deleterious effects of the stomach environment, either by protection of the peptide (or derivative) or by release of the peptide (or derivative) beyond the stomach environment, such as in the intestine. To ensure fall gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

3. Topical Delivery Formulations

Compositions can be applied topically. This does not work well for most peptide formulations, although it can be effective especially if applied to the lungs, nasal, oral (sublingual, buccal), vaginal, or rectal mucosa.

The LIGHT-HVEM antagonists can be delivered to the lungs while inhaling and traverses across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers.

4. Controlled Delivery Polymeric Matrices

Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of LIGHT-HVEM antagonists, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release 5,13-22 (1987); Mathiowitz, et al., Reactive Polymers 6, 275-283 (1987); and Mathiowitz, et al., J. Appl. Polymer Sci. 35, 755-774 (1988).

The devices can be formulated for local release to treat the area of implantation or injection—which will typically deliver a dosage that is much less than the dosage for treatment of an entire body or systemic delivery. These can be implanted or injected subcutaneously, into the muscle, fat, or swallowed.

III. Methods of Manufacture

A. Methods for Producing Polypeptides

Isolated polypeptides can be obtained by, for example, chemical synthesis or by recombinant production in a host cell. To recombinantly produce a costimulatory polypeptide, a nucleic acid containing a nucleotide sequence encoding the polypeptide can be used to transform, transduce, or transfect a bacterial or eukaryotic host cell (e.g., an insect, yeast, or mammalian cell). In general, nucleic acid constructs include a regulatory sequence operably linked to a nucleotide sequence encoding a costimulatory polypeptide. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well know in the art include, for example, *Escherichia coli* strains such as BL-21, and cultured mammalian cells such as CHO cells.

In eukaryotic host cells, a number of viral-based expression systems can be utilized to express polypeptides. Viral based expression systems are well known in the art and include, but are not limited to, baculoviral, SV40, retroviral, or vaccinia based viral vectors.

Mammalian cell lines that stably express variant costimulatory polypeptides can be produced using expression vectors with appropriate control elements and a selectable marker. For example, the eukaryotic expression vectors pCR3.1 (Invitrogen Life Technologies) and p91023(B) (see Wong et al. (1985) Science 228:810-815) are suitable for expression of variant costimulatory polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of an expression vector by electroporation, lipofection, calcium phosphate, or calcium chloride co-precipitation, DEAE dextran, or other suitable transfection method, stable cell lines can be selected (e.g., by antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, polypeptides can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Polypeptides can be isolated using, for example, chromatographic methods such as DEAE ion exchange, gel filtration, and hydroxylapatite chromatography. For example, a polypeptide in a cell culture supernatant or a cytoplasmic extract can be isolated using a protein G column. In some embodiments, polypeptides can be "engineered" to contain an amino acid sequence that allows the polypeptides to be captured onto an affinity matrix. For example, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides.

B. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant costimulatory polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992. Examples of amino acid positions that can be modified include those described herein.

C. Methods for Producing Antibodies

The basic antibody structural unit comprises a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta; or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology, Paul, W., ed., 2nd ed. Raven Press, N.Y., 1989, Ch. 7).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4.

1. Production of Polyclonal Antibodies

Polyclonal antibodies are obtained as sera from immunized animals such as rabbits, goats, rodents, etc. and may be used directly without further treatment or may be subjected to conventional enrichment or purification methods such as ammonium sulfate precipitation, ion exchange chromatography, and affinity chromatography.

2. Production of Monoclonal Antibodies

Monoclonal antibodies may be produced using conventional hybridoma technology, such as the procedures introduced by Kohler and Milstein (Nature, 256:495-97 (1975)), and modifications thereof. An animal, preferably a mouse, is primed by immunization with an immunogen to elicit the desired antibody response in the primed animal. B lymphocytes from the lymph nodes, spleens or peripheral blood of a primed animal are fused with myeloma cells, generally in the presence of a fusion promoting agent such as polyethylene glycol (PEG). Any of a number of murine myeloma cell lines are available for such use: the P3-NS1/1-Ag4-1, P3-x63-k0Ag8.653, Sp2/0-Ag14, or HL1-653 myeloma lines (available from the ATCC, Rockville, Md.). Subsequent steps include growth in selective medium so that unfused parental myeloma cells and donor lymphocyte cells eventually die while only the hybridoma cells survive. These are cloned and grown and their supernatants screened for the presence of antibody of the desired specificity, e.g. by immunoassay techniques. Positive clones are subcloned, e.g., by limiting dilution, and the monoclonal antibodies are isolated.

Hybridomas produced according to these methods can be propagated in vitro or in vivo (in ascites fluid) using techniques known in the art (see generally Fink et al., Prog. Clin. Pathol., 9:121-33 (1984)). Generally, the individual cell line is propagated in culture and the culture medium containing high concentrations of a single monoclonal antibody can be harvested by decantation, filtration, or centrifugation.

a. Production of Chimeric and Humanized Monoclonal Antibodies

Chimeric and humanized antibodies have the same or similar binding specificity and affinity as a mouse or other non-human antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. In some methods, the isotype of the antibody is human IgG1. IgM antibodies can also be used in some methods. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody, (referred to as the donor immunoglobulin). See, Queen et al., Proc. Natl. Acad. Sci. USA 86:10029-10033 (1989), WO 90/07861, U.S. Pat. Nos. 5,693,762, 5,693,761, 5,585,089, 5,530,101, and Winter, U.S. Pat. No. 5,225,539). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 A of a CDR region), or
(4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

b. Production of Human Monoclonal Antibodies

Human antibodies against LIGHT and HVEM can be produced by a variety of techniques described below. Some human antibodies are selected by competitive binding experiments or otherwise, to have the same epitope specificity as a particular mouse antibody. Human antibodies preferably have isotype specificity human IgG1.

One method for producing human monoclonal antibodies is the trioma methodology. The basic approach and an exemplary cell fusion partner, SPAZ-4, for use in this approach have been described by Oestberg et al., Hybridoma 2:361-367 (1983); Oestberg, U.S. Pat. No. 4,634,664; and Engleman et al., U.S. Pat. No. 4,634,666). The antibody-producing cell lines obtained by this method are called triomas, because they are descended from three cells—two human and one mouse. Initially, a mouse myeloma line is fused with a human B-lymphocyte to obtain a non-antibody-producing xenogeneic hybrid cell, such as the SPAZ-4 cell line. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes or bone marrow of a human donor. If antibodies against a specific antigen or epitope are desired, it is preferable to use that antigen or epitope thereof for immunization. Immunization can be either in vivo or in vitro. For in vivo immunization, B cells are typically isolated from a human immunized with LIGHT or HVEM. In some methods, B cells are isolated from the same patient who is ultimately to be administered antibody therapy. For in vitro immunization, B-lymphocytes are typically exposed to antigen for a period of 7-14 days in a media such as RPMI-1640 supplemented with 10% human plasma.

The immunized B-lymphocytes are fused to a xenogeneic hybrid cell such as SPAZ-4 by well known methods. For example, the cells are treated with 40-50% polyethylene glycol of MW 1000-4000, at about 37°0 C., for about 5-10 min. Cells are separated from the fusion mixture and propagated in media selective for the desired hybrids (e.g., HAT or AH). Clones secreting antibodies having the required binding specificity are identified by assaying the trioma culture medium for the ability to bind to LIGHT or HVEM. Triomas producing human antibodies having the desired specificity are subcloned by the limiting dilution technique and grown in vitro in culture medium. The trioma cell lines obtained are then tested for the ability to bind LIGHT or HVEM.

Although triomas are genetically stable they do not produce antibodies at very high levels. Expression levels can be increased by cloning antibody genes from the trioma into one or more expression vectors, and transforming the vector into standard mammalian, bacterial or yeast cell lines.

Human antibodies against LIGHT and HVEM can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/1222, U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741. Transgenic mice are particularly suitable. Anti-LIGHT and anti-HVEM antibodies are obtained by immunizing a transgenic nonhuman mammal with polypeptides corresponding to fill length LIGHT or HVEM polypeptides or immunogenic fragments thereof. Monoclonal antibodies are prepared by, e.g., fusing B-cells from such mammals to suitable myeloma cell lines using conventional Kohler-Milstein technology. Human polyclonal antibodies can also be provided in the form of serum from humans immunized with an immunogenic agent. Optionally, such polyclonal antibodies can be concentrated by affinity purification using LIGHT or HVEM polypeptides or fragments thereof as an affinity reagent.

A further approach for obtaining human anti-LIGHT and anti-HVEM antibodies is to screen a DNA library from human B cells according to the general protocol outlined by Huse et al., Science 246:1275-1281 (1989). As described for trioma methodology, such B cells can be obtained from a human immunized with full length LIGHT or HVEM polypeptides or immunogenic fragments thereof. Optionally, such B cells are obtained from a patient who is ultimately to receive antibody treatment. Antibodies binding to LIGHT, HVEM, or fragments thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047, U.S. Pat. Nos. 5,877,218, 5,871,907, 5,858, 657, 5,837,242, 5,733,743 and 5,565,332). In these methods, libraries of phage are produced in which members display different antibodies on their outer surfaces. Antibodies are usually displayed as Fv or Fab fragments. Phage displaying antibodies with a desired specificity are selected by affinity enrichment to a LIGHT or HVEM polypeptide or fragment thereof.

In a variation of the phage-display method, human antibodies having the binding specificity of a selected murine antibody can be produced (Winter, WO 92/20791). In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for αSyn (e.g., at least $10^8$ and preferably at least $10^9 M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for LIGHT or HVEM are selected. These phage display the variable regions of completely human anti-LIGHT or anti-HVEM antibodies. These antibodies usually have the same or similar epitope specificity as the murine starting material.

The heavy and light chain variable regions of chimeric, humanized, or human antibodies can be linked to at least a portion of a human constant region. The choice of constant region depends, in part, whether antibody-dependent complement and/or cellular mediated toxicity is desired. For example, isotopes IgG1 and IgG3 have complement activity and isotypes IgG2 and IgG4 do not. Choice of isotype can also affect passage of antibody into the brain. Human isotype IgG1 is preferred. Light chain constant regions can be lambda or kappa. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

3. Expression of Recombinant Antibodies

Chimeric, humanized and human antibodies are typically produced by recombinant expression. Recombinant polynucleotide constructs typically include an expression control sequence operably linked to the coding sequences of antibody chains, including naturally associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof (Winnacker, From Genes to Clones, VCH Publishers, NY, 1987). A number of suitable host cell lines capable of secreting intact heterologous proteins have been developed in the art, and include CHO cell lines, various COS cell lines, HeLa cells, L cells, human embryonic kidney cell, and myeloma cell lines. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes including cytomegalovirus, SV40, adenovirus, bovine papillomavirus (Co et al., J. Immunol. 148: 1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, Protein Purification (Springer-Verlag, NY, 1982)).

Polypeptide immunogens disclosed herein can also be linked to a suitable carrier molecule to form a conjugate which helps elicit an immune response. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli, cholera*, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-S-glycerine cysteine (Pam.sub.3Cys), mannan (a manose polymer), or glucan (a beta 1.fwdarw.2 polymer)), cytokines (e.g., IL-1, IL-1 alpha and beta peptides, IL-2, gamma-INF, IL-10, GM-CSF), and chemokines (e.g., MIP1alpha and beta, and RANTES). Immunogenic agents can also be linked to peptides that enhance transport across tissues, as described in O'Mahony, WO 97/17613 and WO 97/17614. Immunogens may be linked to the carries with or with out spacers amino acids (e.g., gly-gly).

Some conjugates can be formed by linking agents to at least one T cell epitope. Some T cell epitopes are promiscuous while other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), Hepatitis B surface antigen, pertussis, toxoid, measles virus F protein, *Chlamydia trachomitis* major outer membrane protein, diphtheria toxoid, *Plasmodium falciparum* circumsporozite T, *Plasmodium falciparum* CS antigen, *Schistosoma mansoni* triose phosphate isomersae, *Escherichia coli* TraT, and Influenza virus hemagluttinin (HA). The immunogenic peptides of the invention can also be conjugated to the T-cell epitopes described in Sinigaglia F. et al., Nature, 336: 778-780 (1988); Chicz R. M. et al., J. Exp. Med., 178:27-47 (1993); Hammer J. et al., Cell 74:197-203 (1993); Falk K. et al., Immunogenetics, 39:230-242 (1994); WO 98/23635; and, Southwood S. et al. J. Immunology, 160:3363-3373 (1998).

Alternatively, the conjugates can be formed by linking agents to at least one artificial T-cell epitope capable of binding a large proportion of MHC Class II molecules., such as the pan DR epitope ("PADRE"). PADRE is described in U.S. Pat. No. 5,736,142, WO 95/07707, and Alexander J et al., Immunity, 1:751-761 (1994). A preferred PADRE peptide is AKX-VAAWTLKAAA, wherein X is preferably cyclohexylalanine, tyrosine or phenylalanine, with cyclohexylalanine being most preferred.

Immunogenic agents can be linked to carriers by chemical crosslinking. Techniques for linking an immunogen to a carrier include the formation of disulfide linkages using N-succinimidyl-3-(2-pyridyl-thio)propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cy-clohexane-1-carboxylic acid. The carboxyl groups can be activated by combining them with succinimide or 1-hydroxyl-2-nitro-4-sulfonic acid, sodium salt.

Immunogenicity can be improved through the addition of spacer residues (e.g., Gly-Gly) between the $T_h$ epitope and the peptide immunogen. In addition to physically separating the $T_h$ epitope from the B cell epitope (i.e., the peptide immunogen), the glycine residues can disrupt any artificial secondary structures created by the joining of the $T_h$ epitope with the peptide immunogen, and thereby eliminate interference between the T and/or B cell responses. The conformational separation between the helper epitope and the antibody eliciting domain thus permits more efficient interactions between the presented immunogen and the appropriate $T_h$ and B cells.

To enhance the induction of T cell immunity in a large percentage of subjects displaying various HLA types to an agent of the present invention, a mixture of conjugates with different $T_h$ cell epitopes can be prepared. The mixture may contain a mixture of at least two conjugates with different $T_h$ cell epitopes, a mixture of at least three conjugates with different $T_h$ cell epitopes, or a mixture of at least four conjugates with different $T_h$ cell epitopes. The mixture may be administered with an adjuvant.

Immunogenic peptides can also be expressed as fusion proteins with carriers (i.e., heterologous peptides). The immunogenic peptide can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N and C termini of the peptide. Some carrier peptides serve to induce a helper T-cell response against the carrier peptide. The induced helper T-cells in turn induce a B-cell response against the immunogenic peptide linked to the carrier peptide.

IV. Methods of Use

A. Reducing or Inhibiting T Cell Activation or Survival

LIGHT-HVEM antagonists, nucleic acids encoding LIGHT-HVEM antagonists, or cells expressing LIGHT-HVEM antagonists can be used to reduce or inhibit the activation of T cells (i.e., decrease antigen-specific proliferation of T cells, decrease cytokine production by T cells, inhibit or reduce differentiation and effector functions of T cells) or to reduce T cell survival.

LIGHT-HVEM antagonists can be used to reduce or inhibit T cell activation and/or survival. The methods can include contacting a T cell with a LIGHT-HVEM antagonists. The contacting can be in vitro ex vivo, or in vivo (e.g., in a mammal such as a mouse, rat, rabbit, dog, cow, pig, non-human primate, or a human).

The contacting can occur before, during, or after activation of the T cell. Typically, contacting of the T cell with LIGHT-HVEM antagonists can after T cell activation. Activation can be, for example, by exposing the T cell to an antibody that binds to the T cell receptor (TCR) or one of the polypeptides of the CD3 complex that is physically associated with the TCR. Alternatively, a T cell can be exposed to either an alloantigen (e.g., a MHC alloantigen) on, for example, an APC [e.g., an interdigitating dendritic cell (referred to herein as a dendritic cell), a macrophage, a monocyte, or a B cell] or an antigenic peptide produced by processing of a protein antigen by any of the above APC and presented to the T cell by MHC molecules on the surface of the APC. The T cell can be a CD4$^+$ T cell or a CD8$^+$ T cell.

The LIGHT-HVEM antagonists can be any of those described herein, including any of the disclosed amino acid alterations, polypeptide fragments, fusion proteins and combinations thereof.

In vitro application of the LIGHT-HVEM antagonists can be useful, for example, in basic scientific studies of immune mechanisms.

B. Therapeutic Uses of LIGHT-HVEM Antagonists

1. Conditions to be Treated

The LIGHT-HVEM antagonists provided herein are generally useful as immune response-reducing therapeutics. In general, the compositions are useful for treating a subject having or being predisposed to any disease or disorder to which the subject's immune system mounts an immune response. The ability of LIGHT-HVEM antagonists to reduce the activation and/or survival of T cells makes the disclosed compositions useful to reduce or inhibit immune responses involving T cells. The terms "treat" and "treating", as used herein includes alleviating, preventing and/or eliminating one or more symptoms associated with inflammatory immune responses, autoimmune disorders or immune responses to grafts, including graft-versus-host disease.

In one embodiment, the compositions and methods disclosed herein are useful for the treatment or prevention of graft rejection or graft versus host disease. The methods and compositions disclosed herein can be used in the prevention or treatment of any type of allograft rejection or graft versus host disease for any type of graft, including a xenograft. The allograft can be an organ transplant, such as, but not limited to, a heart, kidney, liver, lung or pancreas. Alternatively, the allograft can be a tissue transplant, such as, but not limited to, heart valve, endothelial, cornea, eye lens or bone marrow tissue transplant. In yet other embodiments, the allograft can be a skin graft.

In another embodiment, the compositions and methods disclosed herein are useful for the treatment or prevention of inflammatory immune responses and autoimmune disorders. Representative inflammatory and autoimmune disorders that can be treated include, but are not limited to, rheumatoid arthritis, systemic lupus erythematosus, alopecia areata, ankylosing spondylitis, antiphospholipid syndrome, autoimmune addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), inflammatory bowel disease (IBD), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

B. Methods of Treating or Preventing Immunologic Disorders

It has been discovered that LIGHT and HVEM promote T cell activation and survival during immunologic responses. It is believed that LIGHT-HVEM binding of T cells is the mechanism for promoting activation and survival. LIGHT-HVEM antagonists include compounds that inhibit, reduce, or block the biological activity or expression of LIGHT and/or HVEM.

Therefore, one embodiment of a method for treating or inhibiting immunologic disorders, including inflammatory disorders, autoimmune disorders, and immune responses involved in graft rejection, including graft-versus-host disease, is by interfering with the binding of LIGHT to HVEM and by antagonizing their activity. For example, the method can be by administering to a host in need thereof an effective amount of one or more LIGHT-HVEM antagonists. In one embodiment, interference with LIGHT-HVEM binding and associated biological activities is accomplished by providing one or more LIGHT-HVEM antagonists that reduce or inhibit binding of LIGHT to HVEM. In another embodiment, LIGHT and/or HVEM expression is downregulated by providing one or more inhibitory nucleic acids including, but not limited to, ribozymes, triplex-forming oligonucleotides (TFOs), antisense DNA, siRNA, and microRNA specific for nucleic acids encoding LIGHT or HVEM. LIGHT-HVEM antagonists can also be provided in combination with other immunomodulatory agents, such as those described above.

The compositions and methods disclosed herein can be used for prophylactic and therapeutic applications. In prophylactic applications, LIGHT-HVEM antagonists are provided in amounts and frequencies of administration sufficient to eliminate or reduce the risk or delay the outset of immunologic disorders, including physiological, biochemical, histologic and/or behavioral symptoms of the disorder, its complications and intermediate pathological phenotypes presenting during development of the disease or disorder. In therapeutic applications, the compositions and methods disclosed herein are administered to a patient suspected of or already suffering from such an immunologic disease or disorder to treat, at least partially, the symptoms of the disease (physiological, biochemical, histologic and/or behavioral), including its complications and intermediate pathological phenotypes in development of the disease or disorder. An amount adequate to accomplish therapeutic or prophylactic treatment is defined as a therapeutically- or prophylactically-effective amount.

With respect to allograft rejection or graft versus host disease, in a preferred embodiment, the prophylactic methods are initiated prior to transplantation of the allograft. In certain embodiments, the methods can be practiced for a day, three days, a week, two weeks or a month prior to a transplantation. In other embodiments, the drugs are administered for a week, two weeks, three weeks, one month, two months, three months or six months following a transplantation. In a preferred embodiment, the methods are practiced both before and after a transplantation is carried out.

The outcome of the therapeutic and prophylactic methods disclosed herein is to at least produce in a patient a healthful benefit, which includes, but is not limited to, prolonging the lifespan of a patient, prolonging the onset of symptoms of the disorder, and/or alleviating a symptom of the disorder after onset of a symptom of the disorder. For example, in the context of allograft rejection, the therapeutic and prophylactic methods can result in prolonging the lifespan of an allograft recipient, prolonging the duration of allograft tolerance prior to rejection, and/or alleviating a symptom associated with allograft rejection.

C. Methods of Administration of LIGHT-HVEM Antagonists

In some in vivo approaches, a LIGHT-HVEM antagonist itself is administered to a subject in a therapeutically effective amount. Typically, the polypeptides can be suspended in a pharmaceutically-acceptable carrier. Pharmaceutically acceptable carriers are biologically compatible vehicles (e.g., physiological saline) that are suitable for administration to a human. A therapeutically effective amount is an amount of a LIGHT-HVEM antagonist that is capable of producing a medically desirable result (e.g., reduced T cell activation of survival) in a treated animal. LIGHT-HVEM antagonists can be administered orally or by intravenous infusion, or injected subcutaneously, intramuscularly, intraperitoneally, intrarectally, intravaginally, intranasally, intragastrically, intratracheally, or intrapulmonarily. The LIGHT-HVEM antagonists can be delivered directly to an appropriate lymphoid tissue (e.g., spleen, lymph node, or mucosal-associated lymphoid tissue) or directly to an organ or tissue graft.

D. Methods of Administration of Nucleic Acids and Cells

Nucleic acids encoding LIGHT-HVEM antagonists can be administered to subjects in need thereof. Nucleic delivery involves introduction of "foreign" nucleic acids into a cell and ultimately, into a live animal. Several general strategies for gene therapy have been studied and have been reviewed extensively (Yang, N-S., Crit. Rev. Biotechnol. 12:335-356 (1992); Anderson, W. F., Science 256:808-813 (1992); Miller, A. S., Nature 357:455-460 (1992); Crystal, R. G., Amer. J. Med. 92(suppl 6A):44S-52S (1992); Zwiebel, J. A. et al., Ann. N.Y. Acad. Sci. 618:394-404 (1991); McLachlin, J. R. et al., Prog. Nuc. Acid Res. Molec. Biol. 38:91-135 (1990); Kohn, D. B. et al., Cancer Invest. 7:179-192 (1989), which references are herein incorporated by reference in their entirety).

One approach includes nucleic acid transfer into primary cells in culture followed by autologous transplantation of the ex vivo transformed cells into the host, either systemically or into a particular organ or tissue. In one embodiment, vectors containing nucleic acids encoding LIGHT-HVEM antagonists are transfected into cells that are administered to a subject in need thereof.

Ex vivo methods can include, for example, the steps of harvesting cells from a subject, culturing the cells, transducing them with an expression vector, and maintaining the cells under conditions suitable for expression of the variant costimulatory polypeptides provided herein. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject.

Nucleic acid therapy can be accomplished by direct transfer of a functionally active DNA into mammalian somatic tissue or organ in vivo. For example, nucleic acids encoding LIGHT-HVEM antagonists can be administered directly to lymphoid tissues. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs include, for example, those known in the art [see, e.g., Thompson et al. (1992) *Mol. Cell. Biol.* 12:1043-1053; Todd et al. (1993) *J. Exp. Med.* 177: 1663-1674; and Penix et al. (1993) *J. Exp. Med.* 178:1483-1496].

DNA transfer can be achieved using a number of approaches described below. These systems can be tested for successful expression in vitro by use of a selectable marker (e.g., G418 resistance) to select transfected clones expressing the DNA, followed by detection of the presence of the LIGHT-HVEM antagonist expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Examples of successful "gene transfer" reported in the art include: (a) direct injection of plasmid DNA into mouse muscle tissues, which led to expression of marker genes for an indefinite period of time (Wolff, J. A. et al., Science 247:1465 (1990); Acsadi, G. et al., The New Biologist 3:71 (1991)); (b) retroviral vectors are effective for in vivo and in situ infection of blood vessel tissues; (c) portal vein injection and direct injection of retrovirus preparations into liver effected gene transfer and expression in vivo (Horzaglou, M. et al., J. Biol. Chem. 265:17285 (1990); Koleko, M. et al., Human Gene Therapy 2:27 (1991); Ferry, N. et al., Proc. Natl. Acad. Sci. USA 88:8387 (1991)); (d) intratracheal infusion of recombinant adenovirus into lung tissues was effective for in vivo transfer and prolonged expression of foreign genes in lung respiratory epithelium (Rosenfeld, M. A. et al., Science 252: 431 (1991); (e) Herpes simplex virus vectors achieved in vivo gene transfer into brain tissue (Ahmad, F. et al., eds, Miami Short Reports—Advances in Gene Technology: The Molecular Biology of Human Genetic Disease, Vol 1, Boerringer Manneheim Biochemicals, USA, 1991).

Retroviral-mediated human therapy utilizes amphotrophic, replication-deficient retrovirus systems (Temin, H. M., Human Gene Therapy 1:111 (1990); Temin et al., U.S. Pat. No. 4,980,289; Temin et al., U.S. Pat. No. 4,650,764; Temin et al., U.S. Pat. No. No. 5,124,263; Wills, J. W. U.S. Pat. No. 5,175,099; Miller, A. D., U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D. G. et al., Mol. Cell. Biol. 10:4239 (1990). This condition is met by certain of the preferred target cells into which the present DNA molecules are to be introduced, i.e., actively growing tumor cells. Gene therapy of cystic fibrosis using transfection by plasmids using any of a number of methods and by retroviral vectors has been described by Collins et al., U.S. Pat. No. 5,240,846.

Nucleic acid molecules encoding LIGHT-HVEM antagonists may be packaged into retrovirus vectors using packaging cell lines that produce replication-defective retroviruses, as is well-known in the art (see, for example, Cone, R. D. et al., Proc. Natl. Acad. Sci. USA 81:6349-6353 (1984); Mann, R. F. et al., Cell 33:153-159 (1983); Miller, A. D. et al., Molec. Cell. Biol. 5:431-437 (1985),; Sorge, J., et al., Molec. Cell. Biol. 4:1730-1737 (1984); Hock, R. A. et al., Nature 320:257 (1986); Miller, A. D. et al., Molec. Cell. Biol. 6:2895-2902 (1986). Newer packaging cell lines which are efficient and safe for gene transfer have also been described (Bank et al., U.S. Pat. No. 5,278,056).

This approach can be utilized in a site specific manner to deliver the retroviral vector to the tissue or organ of choice. Thus, for example, a catheter delivery system can be used (Nabel, E. G et al., Science 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M. S., In: Virology, Fields, B N et al., eds, Raven Press, New York, 1990, p. 1679; Berkner, K. L., Biotechniques 6:616 9191988), Strauss, S. E., In: The Adenoviruses, Ginsberg, H S, ed., Plenum Press, New York, 1984, chapter 11), herpes simplex virus (HSV) for neuron-specific delivery and persistence. Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R. J. et al., EMBO J. 10:3941 (1991).

Another vector which can express the disclosed DNA molecule and is useful in the present therapeutic setting, particularly in humans, is vaccinia virus, which can be rendered non-replicating (U.S. Pat. Nos. 5,225,336; 5,204,243; 5,155,020; 4,769,330; Sutter, G et al., Proc. Natl. Acad. Sci. USA (1992) 89:10847-10851; Fuerst, T. R. et al., Proc. Natl. Acad. Sci. USA (1989) 86:2549-2553; Falkner F. G. et al.; Nucl. Acids Res (1987) 15:7192; Chakrabarti, S et al., Molec. Cell. Biol. (1985) 5:3403-3409). Descriptions of recombinant vaccinia viruses and other viruses containing heterologous DNA and their uses in immunization and DNA therapy are reviewed in: Moss, B., Curr. Opin. Genet. Dev. (1993) 3:86-90; Moss, B. Biotechnology (1992) 20: 345-362; Moss, B., Curr Top Microbiol Immunol (1992) 158:25-38; Moss, B., Science (1991) 252:1662-1667; Piccini, A et al., Adv. Virus Res. (1988) 34:43-64; Moss, B. et al., Gene Amplif Anal (1983) 3:201-213.

In addition to naked DNA or RNA, or viral vectors, engineered bacteria may be used as vectors. A number of bacterial strains including *Salmonella,* BCG and Listeria monocytogenes (LM) (Hoiseth & Stocker, Nature 291, 238-239 (1981); Poirier, T P et al. J. Exp. Med. 168, 25-32 (1988); (Sadoff, J. C., et al., Science 240, 336-338 (1988); Stover, C. K., et al., Nature 351, 456-460 (1991); Aldovini, A. et al., Nature 351, 479-482 (1991); Schafer, R., et al., J. Immunol. 149, 53-59 (1992); Ikonomidis, G. et al., J. Exp. Med. 180, 2209-2218 (1994)).

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N.-S., et al., Proc. Natl. Acad. Sci. USA 87:9568 (1990); Williams, R. S. et al., Proc. Natl. Acad. Sci. USA 88:2726 (1991); Zelenin, A. V. et al., FEBS Lett. 280:94 (1991); Zelenin, A. V. et al., FEBS Lett. 244:65 (1989); Johnston, S. A. et al., In Vitro Cell. Dev. Biol. 27:11 (1991)). Furthermore, electroporation, a well-known means to transfer genes into cell in vitro, can be used to transfer DNA molecules to tissues in vivo (Titomirov, A. V. et al., Biochim. Biophys. Acta 1088:131 ((1991)).

"Carrier mediated gene transfer" has also been described (Wu, C. H. et al., J. Biol. Chem. 264:16985 (1989); Wu, G. Y. et al., J. Biol. Chem. 263:14621 (1988); Soriano, P. et al., Proc. Natl. Acad. Sci. USA 80:7128 (1983); Wang, C-Y. et al., Proc. Natl. Acad. Sci. USA 84:7851 (1982); Wilson, J. M. et al., J. Biol. Chem. 267:963 (1992)). Preferred carriers are targeted liposomes (Nicolau, C. et al., Proc. Natl. Acad. Sci. USA 80:1068 (1983); Soriano et al., supra) such as immuno-liposomes, which can incorporate acylated mAbs into the lipid bilayer (Wang et al., supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA.

Plasmid DNA used for transfection or microinjection may be prepared using methods well-known in the art, for example using the Quiagen procedure (Quiagen), followed by DNA purification using known methods, such as the methods exemplified herein.

E. Dosages

For LIGHT-HVEM antagonists and nucleic acids encoding LIGHT-HVEM antagonists, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

EXAMPLES

The present invention may be further understood by reference to the following non-limiting examples.

Example 1

Materials and Methods

Mice:

Female C57BL/6J (B6, H-$2^b$), BALB/c (H-$2^d$), and F1 (B6×DBA/2J) (BDF1; H-$2^{b \times d}$) mice were purchased from the National Cancer Institute (Frederick, Md.). C3H.SW mice (C3.SW-H$2^b$/SnJ) were purchased from The Jackson Laboratory (Bar Harbor, Me.). B6-background LIGHT-KO mice were generated in Lieping Chen's laboratory. HVEM-KO mice (H-$2^b$) and 2C TCR transgenic mice were kindly provided by, respectively, Dr. Wayne Hancock and Dr. Larry Pease (Department of Immunology, Mayo Clinic College of Medicine, Rochester, Minn.). Age- and sex-matched 6- to 8-week-old mice were used for all experiments. All the animal experiments described in this manuscript were approved by the Animal Care and Use Committee of the Johns Hopkins University School of Medicine.

Cell Lines and Antibodies:

P815 mouse mastocytoma cells (DBA/2, H-$2^d$) and EL4 mouse T-cell lymphoma cells (B6, H-$2^b$) were purchased from the American Type Culture Collection (Rockville, Md.). All cell lines were maintained in the complete medium under appropriate conditions. Anti-mouse HVEM mAbs (clone; LBH1) were generated by standard techniques as follows. First, Armenian hamsters were immunized subcutaneously (s.c.) and intraperitoneally (i.p.) with 50 μg mouse HVEM-human Fc fusion proteins emulsified with complete Freund's adjuvant (CFA). Fourteen and 28 days later, the hamsters were immunized s.c. and i.p. again with 50 μg mouse HVEM-human Fc fusion protein emulsified with incomplete Freund's adjuvant (IFA). Thirty five days after the initial immunization, the hamsters were injected intravenously with 50 μg mouse HVEM-human Fc, and sacrified 3 days later. Spleen cells from the hamsters were chemically fused with SP2/0 myeloma cells and the hybridomas producing anti-mouse HVEM mAbs were generated by limiting dilution. Control hamster IgG was purchased from Rockland Immunochemicals (Gilbertsville, Pa.). Anti-2C TCR clonotypic mAb was purified from the supernatants of 1B2 hybridoma and further conjugated with phycoerythrin.

Mouse Parent-to-F1 Transfer GVHD Model in Nonirradiated Hosts:

In the non-irradiated parent-to-F1 GVHD model, 5×$10^7$ spleen cells isolated from wild-type (WT) B6 mice, LIGHT-KO mice, or HVEM-KO mice were transferred intravenously into BDF1 recipients on day 0. In some experiments, donor spleen cells were labeled with 5 μM carboxyfluorescein diacetate succinimidyl ester (CFSE; Molecular Probes, Eugene, Oreg.) prior to transfer. In the mice transferred with WT B6 splenocytes, 100 μg anti-HVEM mAb or control hamster IgG was administered intraperitoneally on days 0, 3, and 6. The recipient mice were killed on the indicated days, and the spleen cells were analyzed by flow cytometry and chromium 51 ($^{51}$Cr)-release assay. In the model employing 2C T cells, 1×$10^7$ spleen cells from 2C TCR-transgenic mice were mixed with 3×$10^7$ B6 spleen cells and then transferred intravenously into the BDF1 host on day 0. Recipient mice were subsequently administered 100 μg anti-HVEM mAb or control hamster IgG intraperitoneally on days 0 and 4. On day 7, recipient spleen cells were harvested and assessed for the presence of 2C T cells by flow cytometric analysis using 1B2 clonotypic mAb and anti-CD8 mAb.

Mouse GVHD Models Employing Allogeneic BM Transfer Into Irradiated Recipients:

Three models of GVHD induced by allogeneic bone marrow (BM) transplantation were employed in these studies. First, BDF1 recipient mice, which were preconditioned with lethal irradiation (12 Gy), were injected intravenously with T cell-depleted B6 BM cells (5×$10^6$ cells) with or without B6 T cells (2-3×$10^6$ cells) isolated from either WT or LIGHT-KO mice. T-cell depletion from BM cells and T-cell isolation from spleen cells was performed by MACS systems using anti-Thy1.2 mAb-conjugated microbeads and pan-T cell isolation kits, respectively (Miltenyi Biotec, Auburn, Calif.). In mice transferred with WT B6 T cells, cohorts of mice were intraperitoneally administered 150 μg anti-HVEM mAb or control hamster IgG on days 0, 3, and 6. The survival of recipient mice was monitored daily. In the second model, BALB/c mice were exposed to lethal irradiation (10 Gy) followed by intravenous transfer of T cell-depleted B6 BM cells (5×$10^6$ cells) with or without B6 T cells (1×$10^6$ cells) isolated from WT, LIGHT-KO, or HVEM-KO mice. In this filly major histocompatibility complex (MHC)-mismatched GVHD model, the survival and body weight change of recipient mice were monitored regularly.

The third GVHD model was induced by MHC-matched, minor histocompatibility antigen (miHA)-mismatched BM transfer, B6 mice were exposed to lethal irradiation (10 Gy) and subsequently injected intravenously with 4×$10^6$ T cell-depleted BM cells from C3H.SW mice (H-$2^b$, Ly9.$1^+$) with or without 3×$10^7$ C3H.SW spleen cells. B6 recipient mice injected with C3H.SW spleen cells were intraperitoneally administered either anti-HVEM mAb or control hamster IgG at 100 μg on days 0, 5, 10, 15, 20, and 25. Recipient mice were monitored for survival daily and evaluated for body weight and GVHD clinical score regularly. For scoring, 5 clinical parameters—weight loss, posture, activity, fur texture, and skin integrity (0-2 in each parameter, maximal score of 10)—were used. In the recipient mice that survived long term, reconstitution of host lymphoid tissues by donor cells was assessed by flow cytometry using double staining with Ly9.1 and CD3 or B220. On day 60, cohorts of recipients were killed, and tissues from liver, skin, and intestine were harvested for pathological analysis by hematoxylin and eosin (H&E) staining. Tissue images were observed using an Olympus CH30 microscope (Olympus, Center Valley, Pa.) equipped with a 20×/0.40 numerical aperture (NA) or a 40×/0.65 NA objective lens. Images were acquired using an Olympus DP12 camera and associated image acquisition software, and were processed using Adobe Photoshop CS2 (Adobe Systems, San Jose, Calif.).

Assessment of Division, Apoptosis, and Antihost CTL Activity of Donor Cells:

In the GVHD model of parent-to-F1 transfer, division of donor T cells was assessed by CFSE intensity of H-2K-negative, $CD4^+$, or $CD8^+$ cells in the spleen at the indicated time points. Apoptosis of donor T cells was examined by Annexin V staining of H-2Kd-negative, $CD4^+$, or $CD8^+$ spleen cells at the indicated time points. Donor anti-host CTL activity was examined. Briefly, recipient spleen cells were harvested 10 days after donor cell transfer and, without any in vitro manipulation, were examined for CTL activity against P815 ($H-2^d$) or EL4 ($H-2^b$) by standard 4-hour $^{51}$Cr-release assay.

Statistical Analysis:

For survival data, Kaplan-Meier survival curves were prepared using StatView 5.0 software (SAS Institute, Cary, N.C.), and statistical differences were analyzed using the log-rank (Mantel-Cox) test. P values less than 0.05 were considered significant.

Example 2

Indispensable Role of Donor T Cell-Derived LIGHT in Graft-Versus-Host Disease (GVHD) Pathogenesis To selectively investigate LIGHT functions in GVHD, mice deficient in the Light gene (LIGHT-KO) were employed. Profound activity of donor anti-host MHC Ag ($H-2^d$)-specific CTLs was generated 10 days after transfer of wild-type (WT) B6 mice splenocytes into BDF1 mice (FIG. 1A). In sharp contrast, anti-host CTL activity was completely diminished when LIGHT-KO B6 spleen cells were transferred into BDF1 hosts, indicating a crucial role of donor-derived LIGHT in allo-CTL generation in vivo. LIGHT is expressed and functions on both antigen-presenting cells (APCs) and activated T cells. Therefore, it was important to examine which subset among transferred donor cells is responsible for the effects of LIGHT. To this end, donor cells composed of WT or LIGHT-KO T cells combined with WT or LIGHT-KO non-T cells were subsequently transferred into BDF1 mice. Anti-host CTL activity was completely abrogated when LIGHT-KO T cells were transferred, irrespective of genotypes of coinjected non-T cells (FIG. 1B). In contrast, the mice transferred with WT T cells plus LIGHT-KO non-T cells showed a marginal decrease of CTL activity compared to those injected with WT T and non-T cells. These results strongly indicate that LIGHT associated with donor T cells, rather than APCs, plays an indispensable role in the generation of anti-host CTLs in vivo.

This notion was bolstered by GVHD models induced by allogeneic BM plus T-cell transfer to lethally irradiated recipient mice. First, BDF1 mice exposed to a lethal dose of irradiation were injected with T cell-depleted B6 BM cells, together with either WT or LIGHT-KO B6 T cells. Mice transferred with WT T cells underwent GVHD, and 60% of them died within 70 days, whereas all mice that underwent transfer with LIGHT-KO T cells survived indefinitely (FIG. 1C). In the second model, fully MHC-mismatched BM transfer was employed as a condition of severe GVHD, in which lethally irradiated BALB/c mice were transferred with T cell-depleted B6 BM cells plus either WT or LIGHT-KO B6 T cells. Recipient mice transferred with WT T cells all died within 11 days of severe GVHD along with profound weight loss (FIG. 1D). In contrast, transfer of LIGHT-KO T cells resulted in a significantly prolonged recipient survival along with a transient recovery of body weight following acute collapse by the irradiation and BM transfer. Together, these findings indicate an indispensable role of donor T cell-derived LIGHT in GVHD pathogenesis.

Example 3

Impaired Survival of LIGHT-Deficient Donor T Cells

The cellular mechanisms of the abrogated anti-host CTL activity in LIGHT-KO donor cells was then investigated. The fate of donor T cells following a transfer into BDF1 recipient mice was monitored. After transfer, the percentage and absolute number of LIGHT-KO donor T cells in the recipient spleen were significantly lower than those of WT donor T cells (FIG. 2). The decrease of LIGHT-KO donor T cells was more prominent in $CD8^+$ T cells than $CD4^+$ T cells. Donor T-cell decrease was observed in both hepatic and splenic lymphocytes, suggesting that changes of cellular distribution are not responsible for this finding.

Figure 3A:
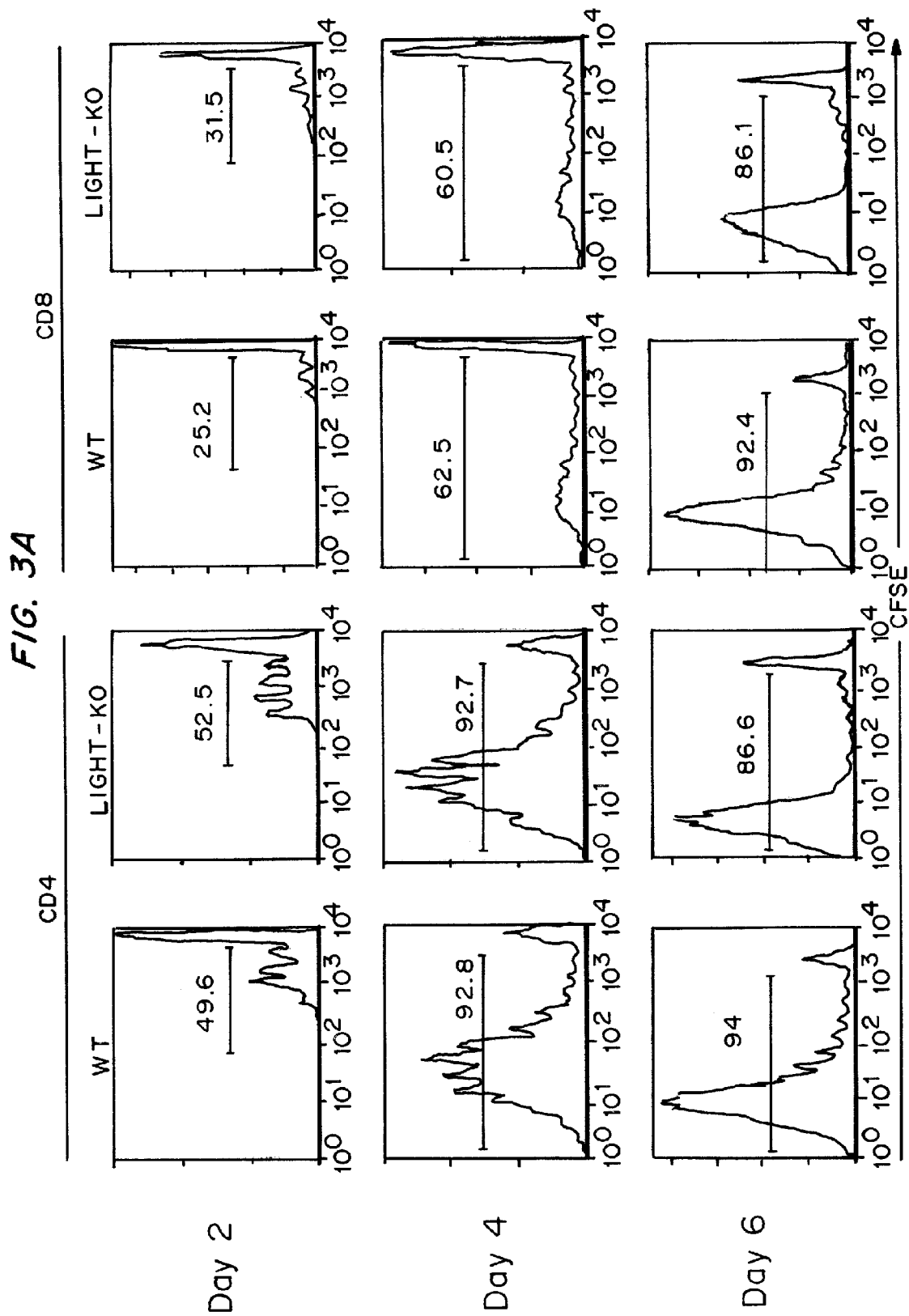
FIG. 3A is a series of histograms showing proliferation of WT or LIGHT-KO B6 donor CD4+ or CD8+ T cells from spleens of recipient BDF1 mice. Proliferation was measured by intensity of CFSE staining of $H-2K^d$-negative, CD4$^+$ or CD8$^+$ cells at days 2, 4 and 6 after injection of donor cells into BDF1 mice. The percentage of donor T cells with more than one division is indicated in each panel.
Figure 3B:
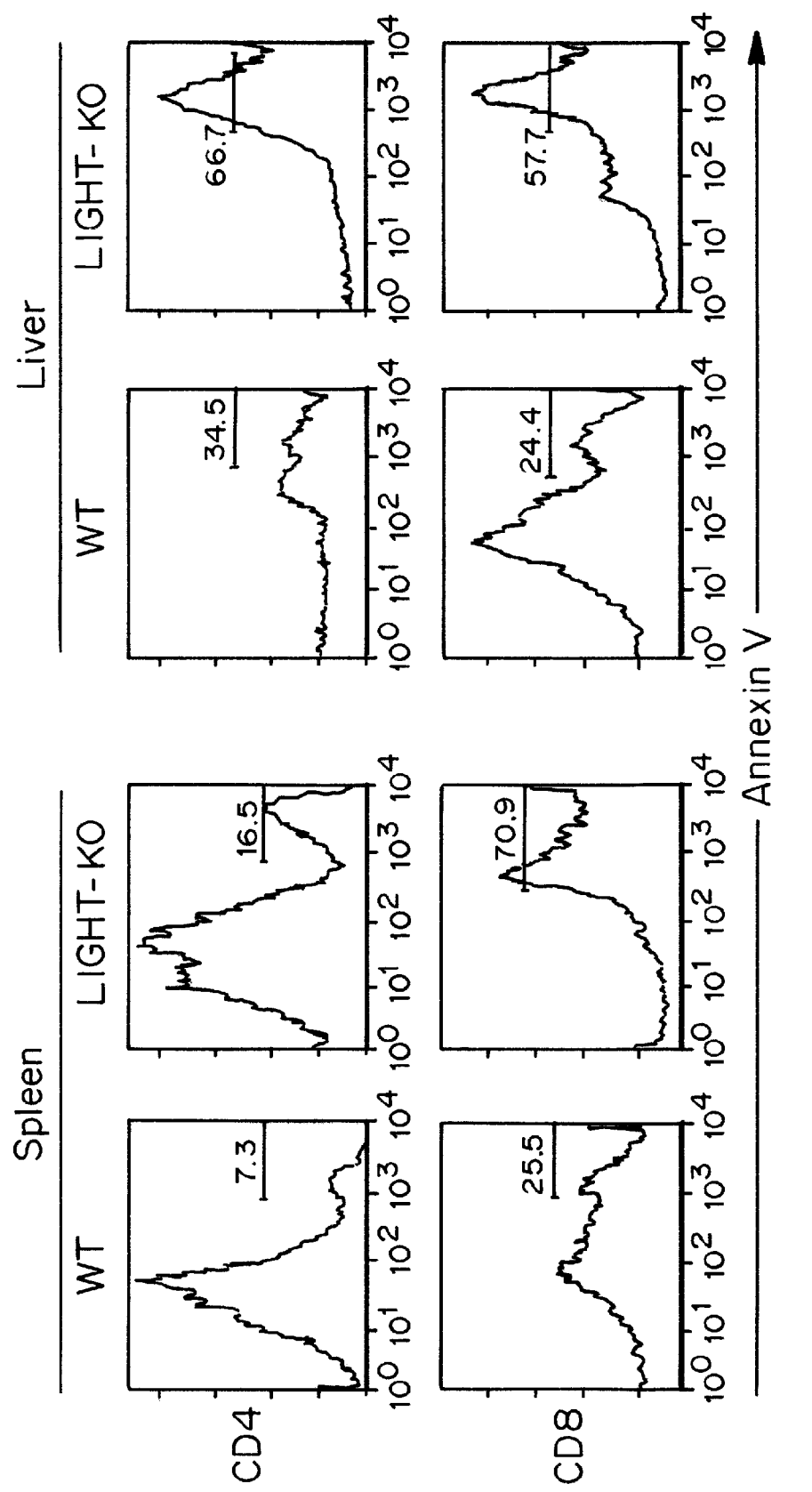
FIG. 3B is a series of histograms showing apoptosis of WT or LIGHT-KO B6 donor CD4+ or CD8+ T cells from spleens of recipient BDF1 mice. Apoptosis was measured by the intensity of Annexin V staining 7 days after injection of donor cells into BDF1 mice. The percentage of Annexin V-positive donor T cells is indicated in each panel.

The decrease of LIGHT-KO donor T cells could be explained by two potential mechanisms: an impairment in proliferation, or an acceleration of cell death. In order to address these possibilities, the expansion kinetics of WT and LIGHT-KO donor T cells in vivo was compared. Two to six days after transfer, division of donor T cells labeled with CFSE was comparable between WT and LIGHT-KO cells in both $CD4^+$ and $CD8^+$ T cells (FIG. 3A). This result indicates a dispensable role of LIGHT in driving the expansion of alloreactive T cells, thus putting into doubt the first possibility. Next, apoptotic cell death in the transferred donor T cells was investigated. In both spleen and liver, the percentage of Annexin V-positive cells in LIGHT-KO donor T cells was significantly increased compared to those of WT T cells (FIG. 3B). Taken together, these findings suggest that deficiency of LIGHT costimulation impairs survival of host-reactive donor T cells by rendering them vulnerable to activation-induced cell death.

Example 4

Essential Role of HVEM on Donor T Cells in Their Survival

Figure 4A:
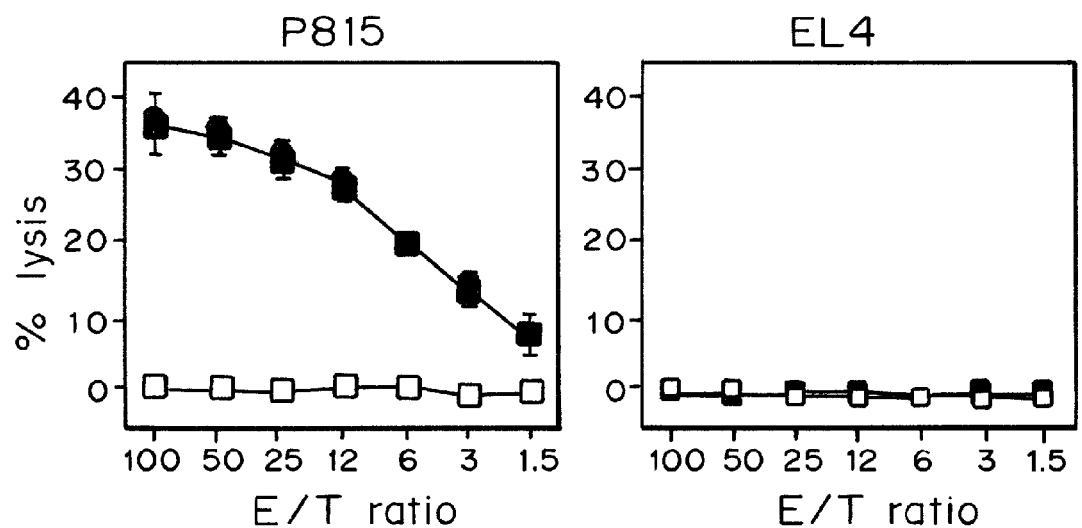
FIG. 4A is a series of line graphs showing anti-host cytotoxic T lymphocyte (CTL) activity of spleen cells isolated from recipient BDF1 ($H-2^d$) mice intravenously injected with either wild-type (WT) or HVEM-KO B6 ($H-2^b$) spleen cells. CTL activity was measured against P815 ($H-2^d$) and EL4 ($H-2^b$) tumor cells by $^{51}$Cr-release assay. Data are expressed as percent lysis as a function of effector cell/target cell ratio. The closed squares represent data obtained using spleen cells from BDF1 mice injected with spleen cells from WT B6 mice and the open squares represent data obtained using spleen cells from BDF1 mice injected with spleen cells from HVEM-KO B6 mice.
Figure 4B:
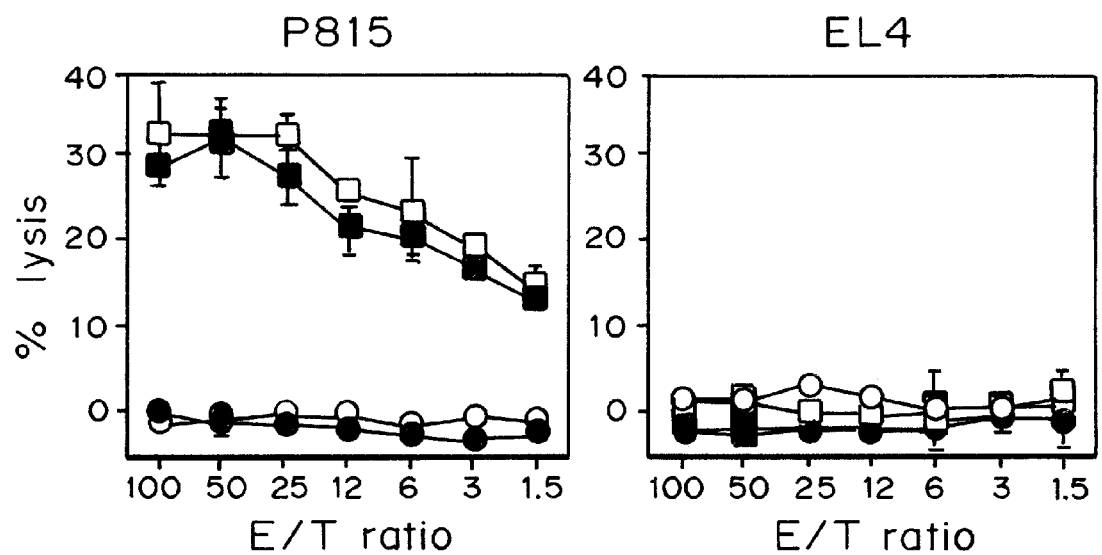
FIG. 4B is a series of line graphs showing anti-host cytotoxic T lymphocyte (CTL) activity of spleen cells isolated from recipient BDF1 ($H-2^d$) mice intravenously injected with various combinations of T cells and non-T cells from either wild-type (WT) or HVEM-KO B6 ($H-2^b$) mice. CTL activity was measured against P815 ($H-2^d$) and EL4 ($H-2^b$) tumor cells by $^{51}$Cr-release assay. Data are expressed as percent lysis as a function of effector cell/target cell ratio, T cells and non-T cells purified from spleen cells of WT or HVEM-KO B6 mice were injected in BDF1 mice in the following combinations: WT T cells plus WT non-T cells (open squares), WT T cells plus HVEM-KO non-T cells (closed squares), HVEM-KO T cells plus WT non-T cells (open circles), and HVEM-KO T cells plus HVEM-KO non-T cells (closed circles).

Among the two functional receptors of LIGHT, HVEM but not LTβR is expressed on T cells and suggested to be responsible for the T cell costimulatory effects of LIGHT. In order to directly address a role of HVEM in GVHD, HVEM-KO lymphocytes were employed as donor cells and transferred into BDF1 recipient mice. No anti-host CTL activity was generated in the mice injected with HVEM-KO cells, in striking contrast to the ample CTL activity induced by a transfer of control lymphocytes (FIG. 4A). Considering the expression and function of HVEM on broad immune populations, including DC, T, and B cells, the functional role of HVEM on donor T and non-T cells was examined using experiments similar to those described in Example 1. Anti-host CTL activity was completely abrogated when HVEM-KO T cells were transferred as donor cells, irrespective of the genotypes of cotransferred non-T cells, whereas a lack of HVEM on non-T cells did not hamper CTL generation when cotransferred with WT T cells (FIG. 4B). These findings indicate that HVEM on donor T cells plays a crucial role in the generation of anti-host CTL in GVHD.

Figure 4C:
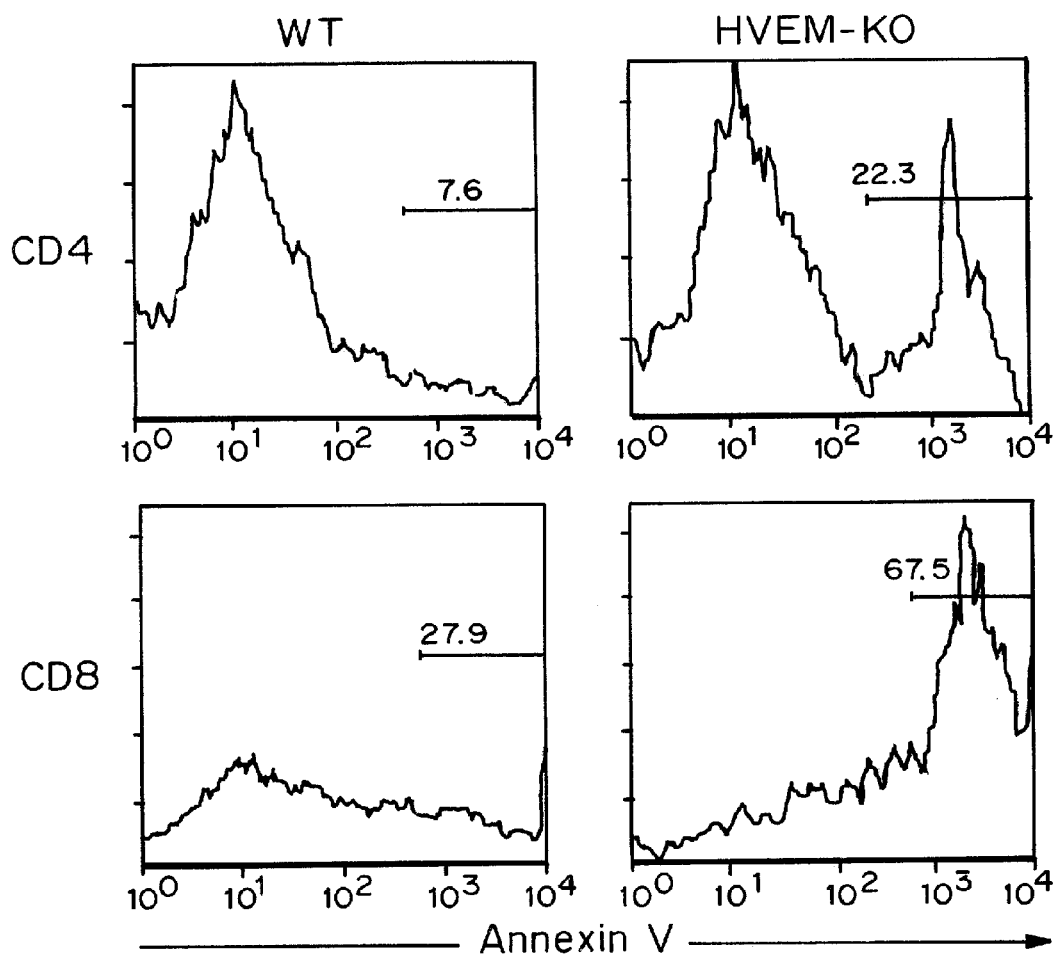
FIG. 4C is a series of histograms showing apoptosis of WT or HVEM-KO B6 donor CD4+ or CD8+ T cells from spleens of recipient BDF1 mice. Apoptosis was measured by the intensity of Annexin V staining 7 days after injection of donor cells into BDF1 mice. The percentage of Annexin V-positive donor T cells is indicated in each panel.
Figure 4D:
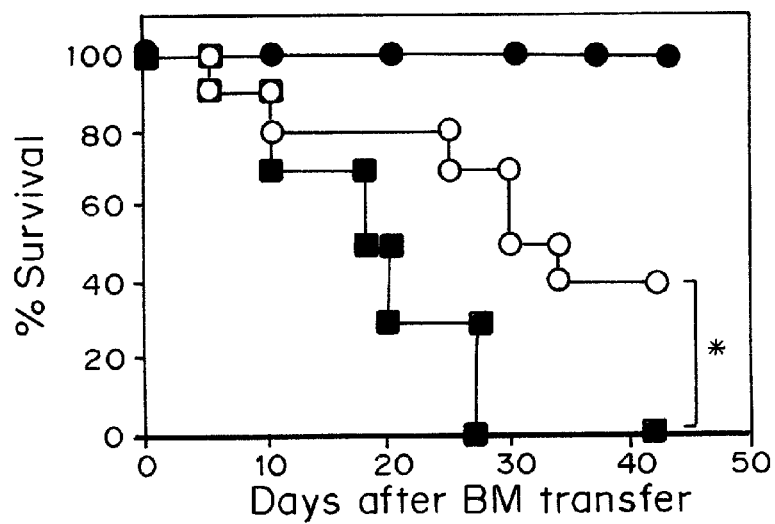
FIG. 4D is a series of line graphs showing survival of BALB/c mice subjected to lethal-dose irradiation (10 Gy) followed by intravenous injection of T cell-depleted B6 BM cells alone (closed circles) or together with WT (closed squares) or HVEM-KO (open circles) B6 T cells. Data are expressed as percent survival as a function of time in days.

HVEM-KO donor T cells undergo massive apoptosis after transfer into the recipient mice and result in a significant decrease of surviving donor T cells (FIG. 4C). These results concur with the findings in LIGHT-KO donor cells, suggesting that HVEM is a receptor responsible for LIGHT effects on donor T-cell survival. The severity of GVHD when HVEM-KO donor T cells are employed in the fully MHC-mismatched BM transfer model was also evaluated. Survival of recipient mice transferred with HVEM-KO cells was significantly prolonged compared to those injected with WT cells (FIG. 4D), highlighting an essential role of donor-derived HVEM in GVHD pathogenesis.

Example 5

Immunotherapy of GVHD by Antagonistic Anti-HVEM mAb

Figure 5A:
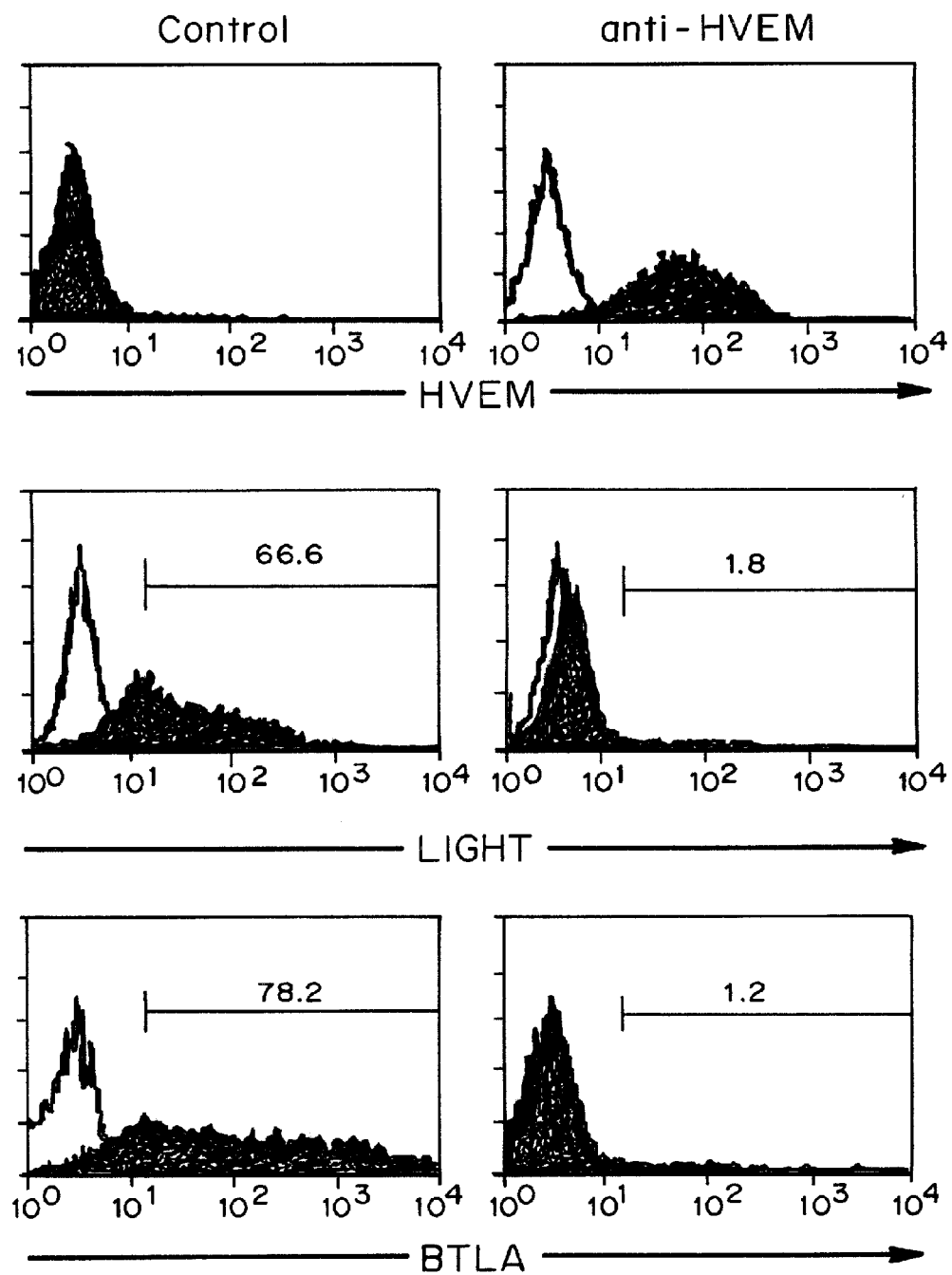
FIG. 5A is a series of histograms showing binding characteristics of the LBH1 mAb. 293T cells transfected with either full-length mouse HVEM (filled histogram) or control vector (open histogram) were stained with LBH1 (right) or control hamster IgG (left), followed by PE-conjugated anti-hamster IgG Ab. Human 293T transfected with full-length mouse LIGHT (middle) or mouse BTLA (bottom) were stained with mouse HVEM-mouse Ig fusion protein (filled histogram) or control mouse Ig protein (open histogram) in the presence of 10 μg/mL LBH1 (right) or control hamster IgG (left). Staining intensity of fusion protein was detected by FITC-conjugated anti-mouse Ig Ab.
Figure 5B:
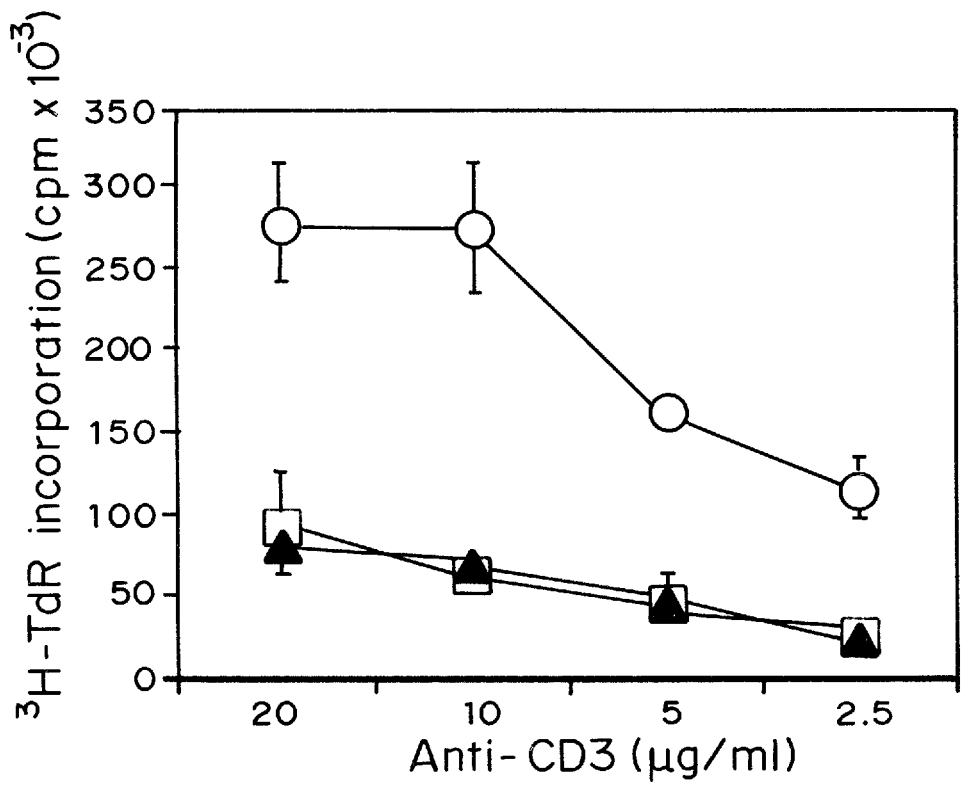
FIG. 5B is a line graph showing the effect of the LBH1 mAb on T cell costimulation. Tissue culture plates were coated with graded doses of anti-CD3 mAb and further with LBH1 (closed triangles) or control hamster IgG (open squares). Purified B6 T cells were cultured in the wells for 3 days, and the proliferation activity during the last 15 hours was measured by $^3$H-thymidine incorporation assay. As positive control, 3 μg/mL anti-CD28 mAb was added in the wells at the beginning of T-cell culture (open circles).
Figure 6A:
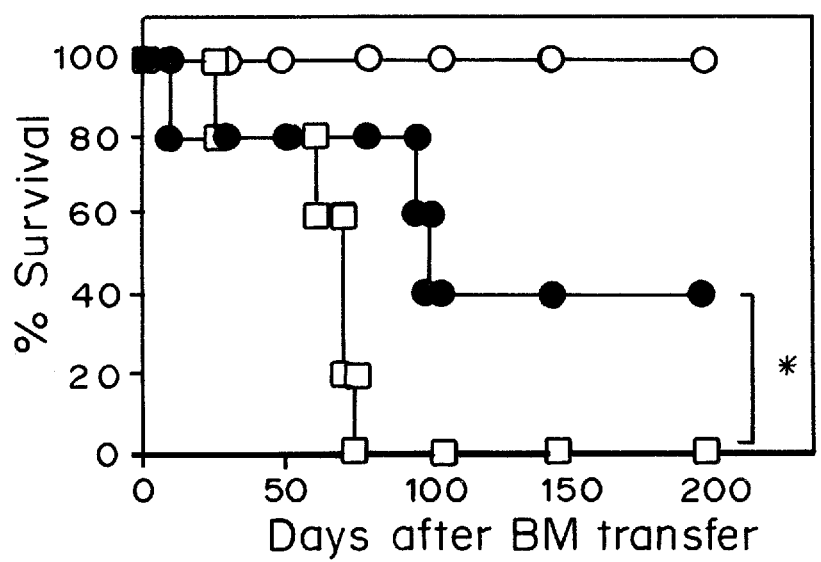
FIG. 6A is line graph showing survival of BDF1 mice subjected to lethal-dose irradiation (12 Gy) followed by intravenous injection of T cell-depleted B6 BM cells alone (open circles) or together with WT B6 T cells. In the groups receiving T cell transfer, the mice were treated intraperitoneally with LBH1 mAb (closed circles) or control hamster IgG (open squares) on days 0, 3 and 6 after BM transfer. Data are expressed as percent survival as a function of time in days.
Figure 6B:
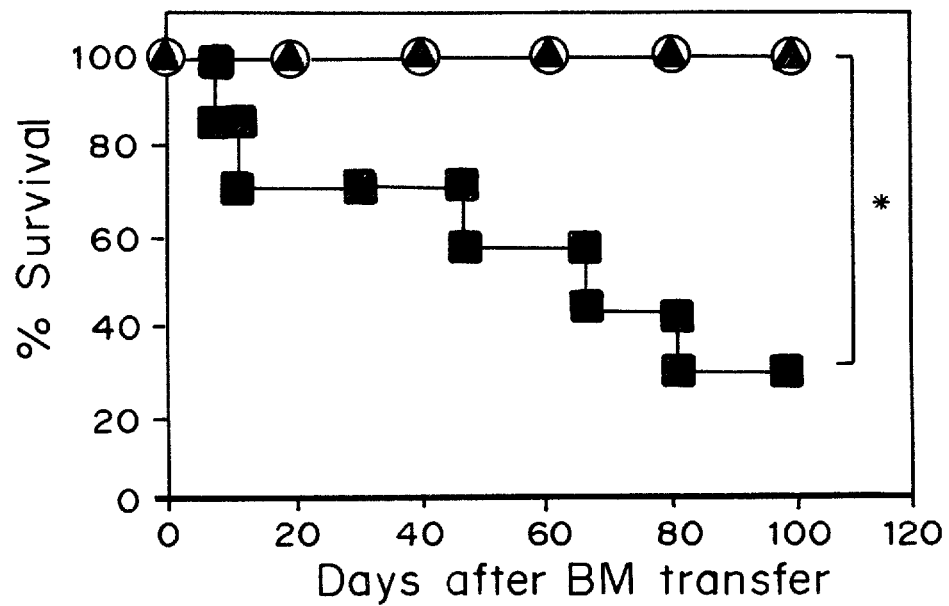
FIG. 6B is a line graph showing survival of B6 mice subjected to lethal-dose irradiation (10 Gy) followed by intravenous injection of T cell-depleted CH3.SW BM cells alone (open circles) or together with CH3.SW spleen cells. In the groups receiving spleen cell transfer, the mice were treated intraperitoneally with LBH1 mAb (closed triangles) or control hamster IgG (closed squares) on days 0, 5, 10, 15, 20 and 25 after BM transfer. Data are expressed as percent survival as a function of time in days.
Figure 6C:
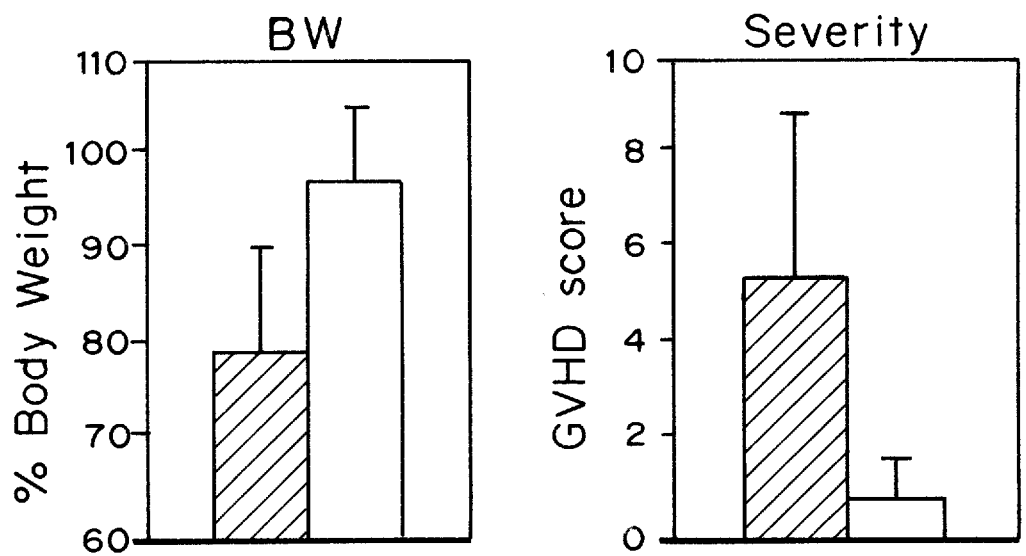
FIG. 6C is a series of bar graphs showing change in body weight or GVHD clinical score. B6 mice were subjected to lethal-dose irradiation (10 Gy) followed by intravenous injection of T cell-depleted CH3.SW BM cells together with CH3.SW spleen cells. The mice were treated intraperitoneally with LBH1 mAb (open bar) or control hamster IgG (filled bar) on days 0, 5, 10, 15, 20 and 25 after BM transfer. Data are expressed as average±standard deviation.

To validate the effects observed in LIGHT-KO or HVEM-KO mice and further extend the findings to the treatment of GVHD with a potential application in the clinical setting, anti-HVEM mAbs interfering with LIGHT-HVEM interactions were developed. One of these mAbs, designated LBH1 was used for further studies. LBH1 abrogates LIGHT-HVEM interactions while it does not deliver a costimutatory signal when used in immobilized form (FIGS. 5A and 5B), indicating that LBH1 is an antagonistic mAb. Therapeutic efficacy of LBH1 on GVHD was investigated by two allogeneic BM transfer models. First, lethally irradiated BDF1 mice were injected with T cell-depleted BM cells together with T cells from B6 mice and subsequently were treated with either LBH1 or control IgG. In this MHC-mismatched model, recipient mice treated with control IgG succumbed to GVHD by day 75, whereas 40% of the mice treated with LBH1 survived more than 200 days (FIG. 6A). In the second model, GVHD was induced by MHC-matched, miHA-mismatched BM transfer. Lethally irradiated B6 mice were injected with T cell-depleted BM cells plus T cells from C3H.SW mice and were further treated with either control IgG or LBH1. In contrast to less than 30% survival in the recipient mice treated with control IgG, all the mice treated with LBH1 survived more than 100 days (FIG. 6B). LBH1-treated mice showed significantly less body weight loss and improved systemic GVHD scores compared with those treated with control IgG (FIG. 6C). After 60 days of BM transfer, control IgG-treated mice displayed a hunched posture and developed severe GVH skin lesions associated with alopecia, crusting, and erosion formation, whereas none of the mice treated with LBH1 exhibited these symptoms. Histologic analysis revealed massive inflammatory cell infiltration of the portal tracts and bile duct injury in the livers of control IgG-treated mice but not those treated with LBH1. Skin of the control IgG-treated mice showed epidermal hyperplasia, thickening of the dermis, loss of hair follicles, and profound cellular infiltration, whereas LBH1 treatment prevented such changes. Further histologic evidence of GVHD was shown by the significant number of apoptotic cells in the intestinal crypt epithelium seen in recipient mice treated with control IgG but not LBH1. In flow cytometric analysis using Ly9.1, which is a cellular marker expressed on C3H.SW but not B6 mice, hematopoictic cells in the LBH1-treated mice were almost completely replaced by donor cells, indicating an accelerated donor hematopoictic chimerism by this therapy. In addition, there was no anti-host CTL activity detected in these long-term surviving mice after LBH1 treatment. Taken together, these results suggest that blockade of the LIGHT-HVEM pathway by antagonistic anti-HVEM mAb effectively ameliorates GVHD associated with allogeneic BM transplantation.

Figure 7A:
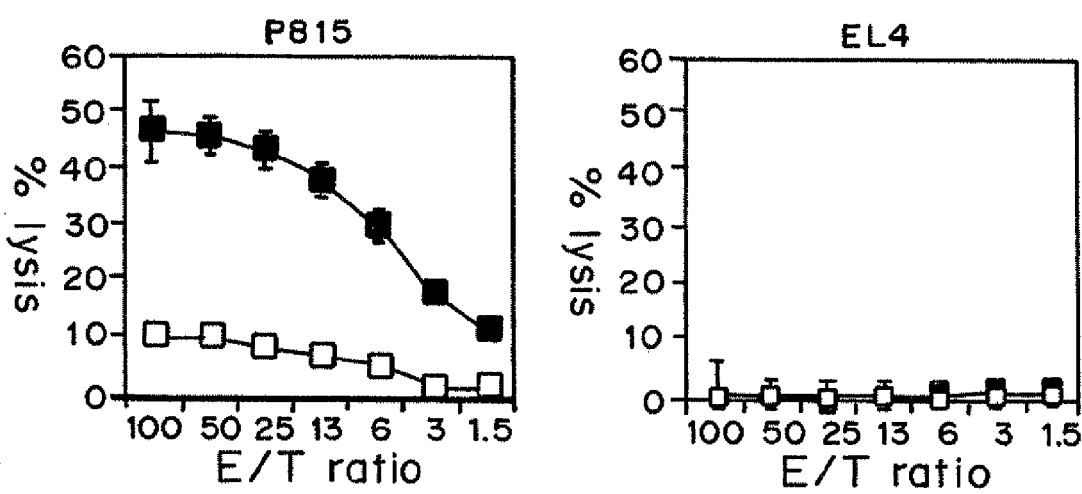
FIG. 7A is a series of line graphs showing anti-host cytotoxic T lymphocyte (CTL) activity of spleen cells isolated from recipient BDF1 ($H-2^d$) mice intravenously injected with WT B6 ($H-2^b$) spleen cells. Mice were treated with intraperitoneal administration of control hamster IgG (closed squares) or LBH1 mAb on days 0, 3 and 6 after spleen cell transfer. CTL activity was measured on day 10 against P815 ($H-2^d$) and EL4 ($H-2^b$) tumor cells by $^{51}$Cr-release assay. Data are expressed as percent lysis as a function of effector cell/target cell ratio.
Figure 7B:
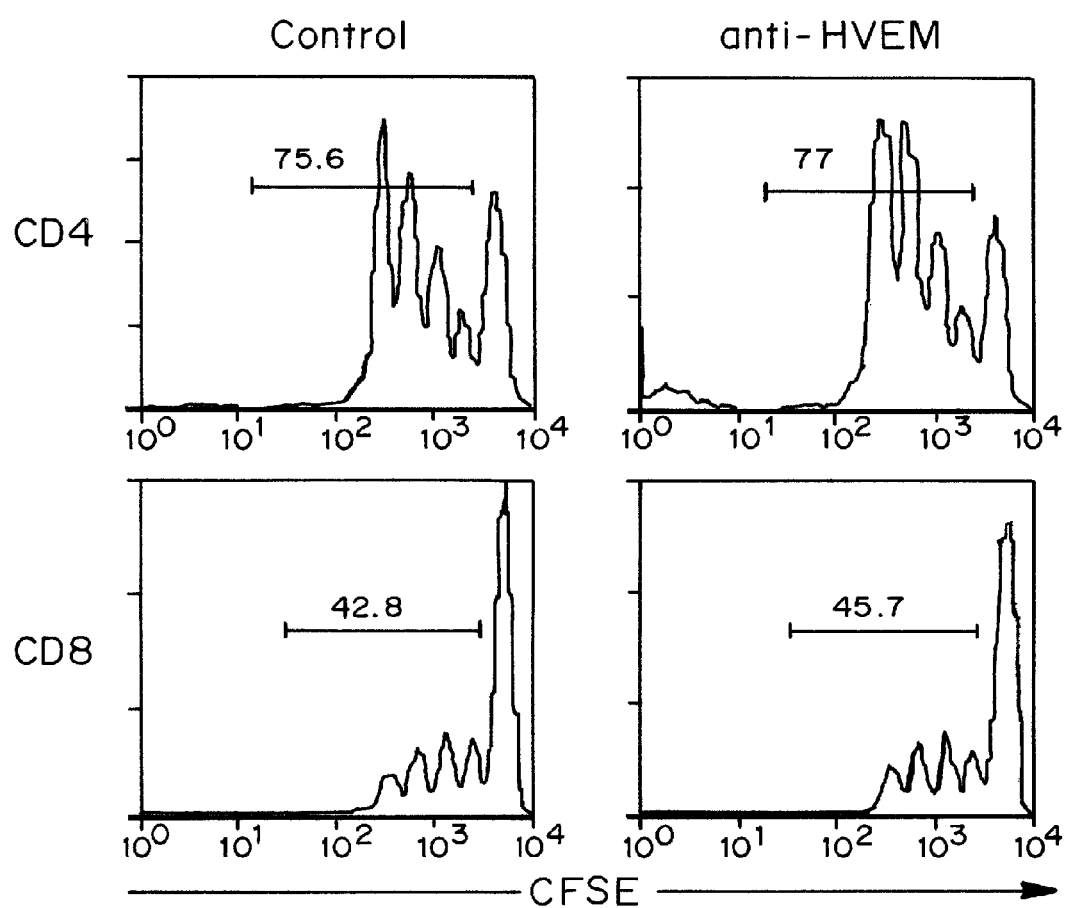
FIG. 7B is a series of histograms showing proliferation of CFSE-labeled B6 donor CD4+ or CD8+ T cells from spleens of recipient BDF1 mice treated with intraperitoneal injections of either control hamster IgG or LBH1 anti-HVEM antibody on days 0 and 3. Proliferation was measured by intensity of CFSE staining of $H-2K^d$-negative, CD4+ or CD8+ cells at days 4 after injection of donor cells into BDF1 mice. The percentage of donor T cells with more than one division is indicated in each panel.

The B6 to BDF1 transfer model was used to investigate the immunologic mechanism of LBH1 therapy. Anti-host CTL activity was profoundly attenuated by the treatments with LBH1 (FIG. 6A). The number of donor T cells was significantly decreased by LBH1 treatment without impairing their division kinetics (FIG. 7B), suggesting that an analogous mechanism found in LIGHT-KO or HVEM-KO donor cells is operating. No significant decrease of the host immune population was detected, indicating that the effects of LBH1 are not ascribed to the nonspecific depletion capacity of this mAb. Finally, by employing $H-2L^d$-reactive 2C TCR-transgenic T cells, the fate of host Ag-specific donor T cells after abrogation of the LIGHT-HVEM costimulatory system was directly monitored. LBH1 treatment of BDF1 recipient mice, which had been transferred with 2C T cells and WT B6 spleen cells, resulted in a significant reduction of 2C T cells in the recipient spleen. This finding suggests that impaired survival of host Ag-specific donor T cells is responsible for the therapeutic effects of LIGHT-HVEM costimulatory blockade in GVHD.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims

We claim:

1. A pharmaceutical composition comprising a LIGHT-HVEM antagonist in an amount effective to reduce or inhibit one or more symptoms associated with graft rejection or graft-versus-host disease in a host, wherein the LIGHT-HVEM antagonist is an antibody to the extracellular portion of HVEM and does not significantly modulate the binding $LT\beta$ to $LT\beta PR$.

2. The pharmaceutical composition of claim 1 further comprising an excipient.

3. The pharmaceutical composition of claim 1, wherein the LIGHT-HVEM antagonist reduces or inhibits the binding of LIGHT to HVEM.

4. The pharmaceutical composition of claim 1, wherein the antibody is a monoclonal antibody.

5. The pharmaceutical composition of claim 4, wherein the antibody has the specificity of the monoclonal antibody LBH1 produced by the hybridoma cell line having ATCC Deposit Number PTA-12171.

6. The pharmaceutical composition of claim 1, wherein the graft is an allograft selected from the group consisting of heart, kidney, liver, lung, pancreas, heart valve, cornea, eye lens, bone marrow tissue or endothelial tissue.

7. A method for treating graft rejection or graft-versus-host disease in a host comprising administering a pharmaceutical composition comprising a LIGHT-HVEM antagonist in an amount effective to reduce or inhibit one or more symptoms associated with graft rejection or graft-versus-host disease in a host, wherein the LIGHT-HVEM antagonist is an antibody to the extracellular portion of HVEM and does not significantly modulate the binding of $LT\beta$ to $LT\beta PR$.

8. The method of claim 7, wherein the LIGHT-HVEM antagonist reduces or inhibits the binding of LIGHT to HVEM.

9. The method of claim 7, wherein the antibody is a monoclonal antibody.

10. The method of claim 9, wherein the antibody has the specificity of the monoclonal antibody LBH1 produced by the hybridoma cell line having ATCC Deposit Number PTA-12171.

11. The method of claim 7, wherein the graft is an allograft selected from the group consisting of heart, kidney, liver, lung, pancreas, heart valve, cornea, eye lens, bone marrow tissue or endothelial tissue.

* * * * *